United States Patent [19]

Mitsuru et al.

[11] 4,269,773
[45] May 26, 1981

[54] FUSED OXAZOLIDINE COMPOUNDS

[75] Inventors: Yoshioka Mitsuru, Toyonaka; Tsuji Teruji, Takatsuki; Nishitani Yasuhiro, Izumi; Nagata Wataru, Nishinomiya, all of Japan

[73] Assignee: Shionogi & Co., Ltd., Japan

[21] Appl. No.: 25,065

[22] Filed: Mar. 29, 1979

Related U.S. Application Data

[62] Division of Ser. No. 790,618, Apr. 25, 1977, Pat. No. 4,159,984.

[30] Foreign Application Priority Data

Apr. 27, 1976 [JP] Japan ................................ 51-49274

[51] Int. Cl.³ .......................................... C07D 498/06
[52] U.S. Cl. ................................ 260/245.4; 546/271; 544/215; 544/238; 544/316; 544/319
[58] Field of Search .................... 260/307 FA, 245.4; 546/271; 544/316, 319

[56]  References Cited

U.S. PATENT DOCUMENTS

| 4,071,512 | 1/1978 | Wolfe | 260/307 FA |
| 4,158,004 | 6/1979 | Koppel | 260/307 F |

OTHER PUBLICATIONS

Yoshioka et al. Chem. Abs. 88, 50635y (1977).

*Primary Examiner*—Mark L. Berch
*Attorney, Agent, or Firm*—Wenderoth, Lind & Ponack

[57] ABSTRACT

Compounds represented by the following formula prepared from 6-aminopenicillanic acid are key intermediates in a stereo-specific synthesis of 1-oxadethiacephalosporins, highly active antibiotics:

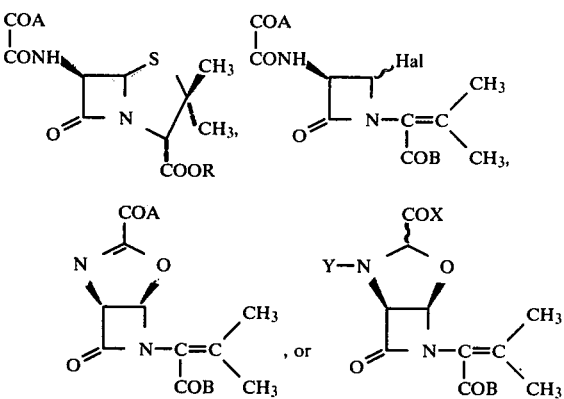

[wherein COA and COB each is carboxy or protected carboxy;
  COX is carboxy, protected carboxy, or a group of the formula $-COCQ=N_2$ or $-COCHQ-Z$ (in which Q is hydrogen, lower alkyl or aryl; and Z is hydrogen or a nucleophilic group);
Hal is halogen;
R is lower alkyl or aralkyl; and
Y is hydrogen or acyl].

11 Claims, No Drawings

FUSED OXAZOLIDINE COMPOUNDS

This is a division of U.S. Pat. No. 4,159,984 application Ser. No. 790,618, filed Apr. 25, 1977.

This invention relates to a new synthetic route along the reactions sequence of the following chart for preparing highly bactericidal 1-oxadethiacephalosporins from penicillins, and literally unknown intermediates thereof.

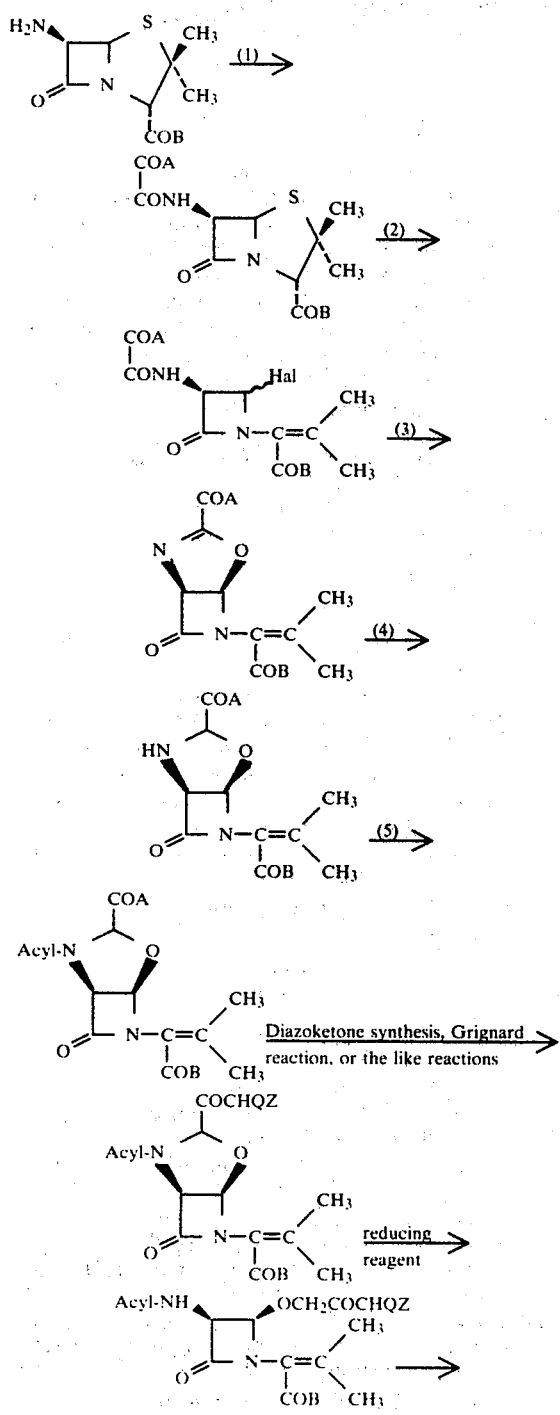

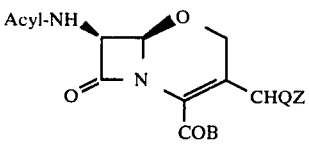

(wherein COA and COB each is carboxy or protected carboxy;
Hal is a halogen;
Q is hydrogen, lower alkyl or aryl; and
Z is a hydrogen or nucleophilic group)

BACKGROUND OF THIS INVENTION

1-Oxadethiacephalosporins have been synthesized from penicillins by Saul Wolfe et al.: Canadian Journal of Chemistry, Volume 52, 3996 (1974); and by total synthesis in Journal of Heterocyclic Chemistry, Volume 5, 779 (1968) by J. C. Sheehan and M. Dadic; German Patent Application OLS (Offenlegungsschrift) No. 2,219,601 (1972); Journal of American Chemical Society, Volume 96, 7582 (1974) and Japanese Patent Application OPI (Kokai) No. 49-133,594 (1974) by B. G. Christensen et al.

The present inventors have found some promising 1-oxadethiacephalosporins and explored a method disclosed in our British Patent Application No. 46,759 filed Nov. 12, 1975.

However, all the methods referred to above were not practical, because of low over-all yield, some by-products separable only difficulty, and long steps to be elaborated.

In order to avoid the formation of stereochemical isomers as by-products, the present inventors conceived a stereoselective synthetic method for preparing said 1-oxadethiacephalosporins.

The method, the embodiment of this invention, is disclosed hereunder in this specification.

COMPOUNDS

The novel intermediates for preparing 1-oxadethiacephalosporins are shown by the following formula:

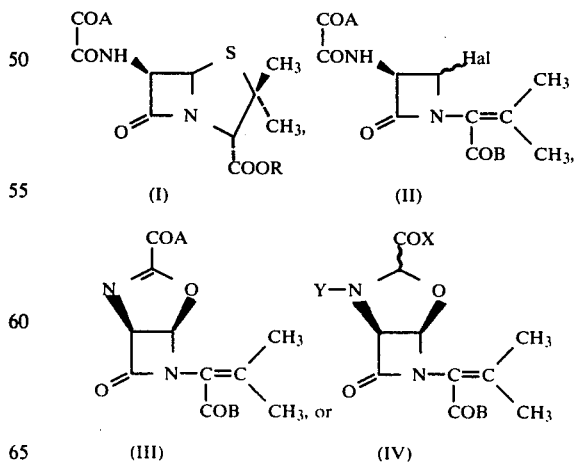

wherein COA and COB each is carboxy or protected carboxy;

COX is carboxy, protected carboxy including halocarbonyl, or a group of the formula: -COCQ=N$_2$ or -COCHQ-Z (in which Q is hydrogen, lower alkyl or aryl; Z is a hydrogen or nucleophilic group);
Hal is halogen;
R is lower alkyl or aralkyl; and
Y is hydrogen or acyl

The Group R is Compound I

The lower alkyl for R includes straight, branched, or cyclic lower alkyl optionally substituted by halogen. Preferable lower alkyl groups are those containing 1 to 8 carbon atoms. Representatives of the specific lower alkyl include methyl, ethyl, isopropyl, butyl, isobutyl, t-butyl, pentyl, 1-methylcyclohexyl, cyclopropylmethyl, cyclopropylethyl, cyclohexyl, cycloheptyl, chloromethyl, chloroethyl, bromoethyl, iodoethyl, trichloroethyl, chlorocyclohexyl, chlorocyclopentyl, bromocycloheptyl, and bromooctyl. The lower aralkyl for R includes mono-, di-, or tricyclic aralkyl groups optionally substituted by an inert group (e.g. lower alkyl, haloalkyl, cyano, aminoalkyl, hydroxy, alkoxy, acyloxy, aralkoxy, nitro, or halogen). Preferable aralkyl groups contain from 6 to 20 carbon atoms. Representatives of the specific aralkyl include benzyl, methoxybenzyl, nitrobenzyl, diphenylmethyl, di-(p-methoxyphenyl)methyl, trityl, phthalidyl, tolyl, xylyl, dihydroanthryl, anthrylmethyl, furylmethyl, thienylmethyl, quinolylmethyl, pyridylmethyl, pyrimidylethyl, and isoxazolylpropyl.

Most preferable R are $C_1$ to $C_3$ alkyl and chloroalkyl, benzyl, methoxybenzyl, nitrobenzyl, diphenylmethyl, and tolymethyl.

Halogen Hal in Compound II

The halogen for Hal is chlorine, bromine, or iodine, in which chlorine is the most preferable.

Acyl group for Y in Compound IV

The acyl group for Y includes a monovalent acyl group derived from inorganic or organic acid and preferably those constituting the side chain of natural or synthetic penicillins or cephalosporins reactive group if any can be protected in a conventional manner.

Representative acyl group can be selected from the following groups:

(1) $C_1$ to $C_{10}$ alkanoyl;
(2) $C_1$ to $C_5$ haloalkanoyl;
(3) azidoacetyl or cyanoacetyl;
(4) acyl groups of the following formula:

$$Ar-CQ^1Q^2-CO-$$

[in which $Q^1$ and $Q^2$ each is hydrogen or methyl and Ar is phenyl, dihydrophenyl, or monocyclic heteroaromatic group containing from 1 to 4 hetero ring atoms selected from N, O, and/or S atoms, and each can optionally be substituted by an inert group [e.g. $C_1$ to $C_5$ alkyl, trifluoromethyl, cyano, aminomethyl, optionally protected carboxymethylthio, carboxy, hydroxy, $C_1$ to $C_3$ alkoxy, $C_1$ to $C_{10}$ acyloxy, $C_7$ to $C_{10}$ aralkoxy, chlorine, bromine, iodine, fluorine, nitro];
(5) (4-pyridon-1-yl)acetyl or (2-iminothiazolin-4-yl)acetyl;
(6) acyl groups of the following formula:

$$Ar-G-CQ^1Q^2-CO-$$

[in which Ar, $Q^1$, and $Q^2$ are defined above and G is O or S atom];
(7) acyl groups of the following formula:

$$Ar-CHT-CO-$$

[in which Ar is as defined above and T is
(i) hydroxy or $C_1$ to $C_{10}$ acyloxy;
(ii) carboxy, $C_2$ to $C_7$ alkoxycarbonyl, $C_2$ to $C_{15}$ aralkoxycarbonyl, $C_1$ to $C_{12}$ aryloxycarbonyl, $C_1$ to $C_7$ alkanoyloxy-$C_1$ to $C_3$ alkoxycarbonyl, cyano, or carbamoyl; or
(iii) sulfo or $C_1$ to $C_7$ alkoxysulfonyl];
(8) acyl groups of the following formula:

$$Ar-CH-CO- \\ | \\ W^1-N-W^2$$

in which Ar is as defined above and
$W^1$ and $W^2$ each is hydrogen or amino substituent [including $C_2$ to $C_{10}$ alkoxycarbonyl, $C_3$ to $C_{10}$ cycloalkyl-$C_2$ to $C_3$-alkoxycarbonyl, $C_5$ to $C_8$ cycloalkoxycarbonyl, $C_1$ to $C_4$ alkylsulfonyl-$C_1$ to $C_4$-alkoxycarbonyl, halo-$C_1$ to $C_3$-alkoxycarbonyl, $C_1$ to $C_{15}$ aralkoxycarbonyl, $C_1$ to $C_{10}$ alkanoyl, or $C_2$ to $C_{15}$ aroyl, each optionally substituted by an inert group (e.g. hydroxy, $C_1$ to $C_5$ alkyl, $C_1$ to $C_{10}$ alkanoyloxy, halogen, $C_1$ to $C_3$ hydroxyalkyl, trifluoromethyl); pyronecarbonyl, thiopyronecarbonyl, pyridonecarbonyl, carbamoyl, guanidinocarbonyl, optionally substituted ureidocarbonyl (e.g. 3-methyl-2-oxoimidazolidin-1-ylcarbonyl, 3-methanesulfonyl-2-oxoimidazolidin-1-ylcarbonyl, 3-methylureidocarbonyl, 1-methylureidocarbonyl), optionally substituted aminooxalylcarbamoyl (e.g. 4-methyl-2,3-dioxopiperazin-1-ylcarbonyl, 4-ethyl-2,3-dioxopiperazin-1-ylcarbonyl) optionally substituted thioureidocarbonyl equivalents of above ureidocarbonyl or aminooxalylcarbamoyl], or $W^1$, $W^2$, and the nitrogen atom combined together represent phthalimido, maleimido, or enamino derived from enolizable carbonyl compound (e.g. $C_5$ to $C_{10}$ acetoacetates, $C_4$ to $C_{10}$ acetoacetamides, acetoacetanilides, acetylacetone, acetoacetonitrile, α-acetyl-γ-butyrolacetone, 1,3-cyclopentanedione);
(9) acyl groups of the following formula:

$$Ar-C-CO- \\ \| \\ NOE$$

(in which Ar is defined above and
E is hydrogen or $C_1$ to $C_5$ alkyl);
(10) 5-aminoadipoyl, N-protected 5-aminoadipoyl (protected by e.g. $C_1$ to $C_{10}$ alkanoyl, up to $C_{10}$ aralkanoyl, $C_2$ to $C_{11}$ aroyl, $C_1$ to $C_5$ haloalkanoyl, or $C_2$ or $C_{11}$ alkoxycarbonyl), or
5-aminoadipoyl protected at the carboxy (protected by e.g. $C_1$ to $C_5$ alkyl, $C_2$ to $C_{21}$ aralkyl, up to $C_{10}$ aroyl, $C_2$ to $C_{10}$ trialkylsilyl, $C_2$ to $C_5$ dialkyl-$C_1$ to $C_5$-alkoxy silyl, and
each protecting group for amino or carboxy can optionally be substituted by $C_1$ to $C_5$ alkyl, $C_1$ to $C_5$ alkoxy, halogen, or nitro; and
(11) acyl groups of the following formula:

L—O—CO—

[in which L is an easily removable and optionally substituted $C_1$ to $C_{10}$ hydrocarbyl group (e.g. t-butyl, 1,1-dimethylpropyl, cyclopropylmethyl, 1-methylcyclohexyl, isobornyl, 2-$C_1$ to $C_2$-alkoxy-t-butyl, 2,2,2-trichloroethyl, benzyl, naphthylmethyl, p-methoxybenzyl, pyridylmethyl, diphenylmethyl)].

Typical examples of Ar in said definitions include furyl, thienyl, pyrryl, oxazolyl, isoxazolyl, oxadiazolyl, oxatriazolyl, thiazolyl, isothiazolyl, thiadiazolyl, thiatriazolyl, pyrazolyl, imidazolyl, triazolyl, tetrazolyl, phenyl, pyridyl, pyrimidyl, pyrazinyl, pyridazinyl, triazinyl, dihydrophenyl, each optionally be substituted by halogen, $C_1$ to $C_5$ alkyl, hydroxy, $C_1$ to $C_5$ acyloxy, $C_7$ to $C_{15}$ aralkoxy e.g. benzyloxy, methoxybenzyloxy, aminobenzyloxy), aminomethyl, $C_1$ to $C_5$ alkoxy and $C_7$ to $C_{12}$ aralkoxycarbonyl.

Representatives of the monovalent specific acyl groups include formyl, acetyl, propionyl, butyryl, isobutyryl, isovaleryl, t-valeryl, hexanoyl, heptanoyl, octanoyl, cyclopentylcarbonyl, cyclopentylacetyl, cyclohexylcarbonyl, cyclohexylacetyl, cyclohexylpropionyl, cyclohexadienylcarbonyl, cyclohexadienylacetyl, cycloheptylcarbonyl, cycloheptylacetyl, cycloheptylpropionyl, chloroacetyl, chloropropionyl, fluoroacetyl, bromoacetyl, difluoroacetyl, dichloroacetyl, dibromoacetyl, trifluoroacetyl, trichloroacetyl, chloropropionyl, acryl, methacryl, butenoyl, hexenoyl, methoxyacetyl, isopropoxyacetyl, pentyloxyacetyl, hexyloxyacetyl, cyclohexyloxyacetyl, cyclohexadienyloxyacetyl, phenoxyacetyl, phenoxypropionyl, phenoxybutyryl, diphenoxyacetyl, methylthiophenoxyacetyl, carboxymethylphenoxyacetyl, sulfophenoxyacetyl, tetrahydronaphthyloxyacetyl, methylthioacetyl, butylthioacetyl, allylthioacetyl, propenylthioacetyl, cyclohexylthioacetyl, cyclohexadienylthioacetyl, phenylthioacetyl, phenylthiopropionyl, fluorophenylthioacetyl, chlorophenylthioacetyl, carboxymethylphenylthioacetyl, pyridylthioacetyl, pyrimidylthioacetyl, benzoyl, methylbenzoyl, dimethylbenzoyl, carboxybenzoyl, aminobenzoyl, methoxybenzoyl, chlorobenzoyl, guanidylaminobenzoyl, dimethoxybenzoyl, trimethoxybenzoyl, methylenedioxybenzoyl, phenylbenzoyl, naphthoyl, methylnaphthoyl, methoxynaphthoyl, ethoxynaphthoyl, tetrahydronaphthoyl, acetylnaphthoyl, furylcarbonyl, thienylcarbonyl, isoxazolylcarbonyl, phenylisoxazolylcarbonyl, dimethylisoxazolylcarbonyl, methylbutylisoxazolylcarbonyl, phenylmethylisoxazolylcarbonyl, chlorophenylmethylisoxazolylcarbonyl, dichlorophenylmethylisoxazolylcarbonyl, chlorofluorophenylisoxazolylcarbonyl, guanidylphenylisoxazolylcarbonyl, guanidylaminophenylfurylisoxazolylcarbonyl, carboxyquinolylcarbonyl, carboxyquinoxalinylcarbonyl, phenylacetyl, phenylpropionyl, phenylbutyryl, hydroxyphenylacetyl, methoxyphenylacetyl, acetyloxyphenylacetyl, aminophenylacetyl, fluorophenylacetyl, chlorophenylacetyl, bromophenylacetyl, methylthiophenylacetyl, sulfophenylacetyl, carboxymethylphenylacetyl, methylphenylacetyl, dimethylphenylacetyl, aminomethylphenylacetyl, acetaminomethylphenylacetyl, diphenylpropionyl, triphenylacetyl, guanidylaminophenylacetyl, guanidylcarbamoylphenylacetyl, tetrazolylphenylacetyl, cinnamoyl, phenylethynylcarbonyl, naphthylacetyl, tetrahydronaphthylacetyl, furylacetyl, nitrofurylacetyl, thienylacetyl, methylthienylacetyl, chlorothienylacetyl, methoxythienylacetyl, sulfothienylacetyl, carboxymethylthienylacetyl, oxazolylacetyl, isoxazolylacetyl, methylisoxazolylacetyl, chlorophenylmethylisoxazolylacetyl, isothiazolylacetyl, imidazolylacetyl, thiadiazolylacetyl, chlorothiadiazolylacetyl, methylthiadiazolylacetyl, methoxythiadiazolylacetyl, tetrazolylacetyl, benzofurylacetyl, benzothienylacetyl, indolylacetyl, pyridylacetyl, α-phenyl-α-fluoroacetyl, α-chlorophenylacetyl, α-bromophenylacetyl, α-sulfophenylacetyl, α-phosphophenylacetyl, α-azidophenylacetyl, mandeloyl, O-formylmandeloyl, α-thienylglycolyl, α-chlorothienylglycolyl, α-thiazolylglycolyl, α-isothiazolylglycolyl, α-thiadiazolylglycolyl, α-oxadiazolylglycolyl, α-benzothienylglycolyl, α-phenylmalonyl, α-thienylmalonyl, α-furylmalonyl, is α-thiazolylmalonyl, α-isothiazolylmalonyl, α-oxadiazolylmalonyl, α-isothiazolylmalonyl, α-thiadiazolylmalonyl, α-benzothienylmalonyl, α-isothiazolyl-α-sulfoacetyl, α-phenylglycyl, α-phenyl-N-methylglycyl, N-sulfo-α-phenylglycyl, N-methyl-N-sulfo-α-phenylglycyl, α-chlorophenylglycyl, α-hydroxyphenylglycyl, α-aminophenylglycyl, α-dichlorophenylglycyl, α-chlorohydroxyphenylglycyl, α-thienylglycyl, α-isooxazolylglycyl, α-pyridylglycyl, α-benzothiazolylglycyl, α-hydroxyiminophenylacetyl, α-methoxyiminophenylacetyl, methoxycarbonyl, ethoxycarbonyl, t-butoxycarbonyl, cyclohexyloxycarbonyl, chloroethoxycarbonyl, trichloroethoxycarbonyl, tribromoethoxycarbonyl, bromoethoxycarbonyl, iodoethoxycarbonyl, cyclopropylmethoxycarbonyl, cyclopropylethoxycarbonyl, cyclopentyloxycarbonyl, cyclohexyloxycarbonyl, cycloheptyloxycarbonyl, cyclohexadienyloxycarbonyl, isobornyloxycarbonyl, methanesulfonylethoxycarbonyl, ethanesulfonylpropoxycarbonyl, phenoxycarbonyl, methylphenoxycarbonyl, dimethylphenoxycarbonyl, diphenylmethoxycarbonyl, naphthyloxycarbonyl, benzyloxycarbonyl, bromobenzyloxycarbonyl, chlorobenzyloxycarbonyl, nitrobenzyloxycarbonyl, methoxybenzyloxycarbonyl, dimethylbenzyloxycarbonyl, methylenedioxybenzyloxycarbonyl, furyloxycarbonyl, pyridylmethoxycarbonyl, quinolyloxycarbonyl, aminoadipoyl, acetylaminoadipoyl, benzoylaminoadipoyl, trichloroethoxycarbonylaminoadipoyl, carbobenzoxyaminoadipoyl, oxoadipoyl, trimethylsilylaminoadipoyl, trimethylsilyloxycarbonyltrimethylsilylaminopentanoyl, carboxybutyryl, methanesulfonyl, ethanesulfonyl, benzenesulfonyl, methylbenzenesulfonyl, and benzylsulfonyl.

The acyl group in Y of Compound IV is a protective group for the reactions, and if required removable at a desired stage of synthesis for exchanging with another acyl suitable for the use of the final 1-oxadethiacephalosporins. In other words, easily introducable and removable groups are preferable ones of the groups. The procedures for the introduction and removal of such groups are well documented in the field of β-lactam chemistry. From other aspect, the acyl group can be widely changed within the gist of this invention. When the acyl group has a reactive functional group, the latter can be protected by conventional methods and afterwards deprotected to give desired acyls.

Some of the most preferable acyl groups for Y include phenylacetyl, phenoxyacetyl, benzoyl, toluoyl, carbobenzoxy, and benzylsulfonyl. Another preferable acyl group for Y is one of most preferable side chain in the objective 1-oxadethiacephalosporins. Reactive functional group if any can be protected by conventional manners. Representatives of them are α-phenyl- α-benzyloxycarbonylacetyl, α-p-hydroxyphenyl-α-diphenylmethoxycarbonylacetyl, α-p-acyloxyphenyl-α-benzyloxycarbonylacetyl, α-p-benzyloxyphenyl-α-t-butoxycarbonylacetyl, α-p-benzyloxyphenyl-α-indanyloxycarbonylacetyl, and α-p-tolylmethoxyphenyl-α-tolyloxy-carbonylacetyl.

Protected Carboxy Group COA, COB, and COX for Compounds I, II, III, and IV

The protected carboxy for COA in Compounds I, COA and COB in Compounds II and III, and COB and COX in Compounds IV include those forming salts including alkali metal salts, alkaline earth metal salts, salts with organic bases; esters including lower alkyl esters, aralkyl esters, aryl esters, organometallic esters, acid anhydrides; acid halides; thiol esters; thiono esters; amides; hydrazides; azide; and like carboxy derivatives.

The protective part of the protected carboxy groups contain preferably up to 20 carbon atoms including optional substituent e.g. alkyl, acyl, carboxy, protected carboxy, hydroxy, alkoxy, aryloxy, aralkyloxy, acyloxy, alkylthio, arylthio, aralkylthio, acylthio, alkylsulfinyl, alkylsulfonyl, arylsulfonyl, amino, alkylamino, arylamino, acylamino, nitro, and halogen, and can further be unsaturated.

Representatives of the specific protected-carboxy groups include those forming salts (e.g. lithium, sodium, potassium, magnesium, calcium, acetoxycalcium, stearoyloxycalcium, trimethylammonium, triethylammonium, dicyclohexylammonium, morpholinium, N-methylmorpholinium, pyridinium, quinolinium, picolinium, and collidinium salts), esters (e.g. methyl, ethyl, propyl, iso-propyl, butyl, t-butyl, 1,1-dimethylpropyl, cyclopropylmethyl, cyclopropylethyl, cyclopentylmethyl, cyclopentyl, cyclohexyl, cycloheptyl, norbornyl, bornyl, vinyl, propenyl, butenyl, pentenyl, pentynyl, 1,1-dimethylpropargyl, tetrahydrofuryl, tetrahydropyranyl, dihydropyranyl, chloromethyl, bromomethyl, iodoethyl, trichloromethyl, trichloroethyl, tribromoethyl, methoxymethyl, ethoxymethyl, ethoxyethyl, t-butoxymethyl, t-butoxyethyl, methoxyvinyl, 1-dimethylamino-3,3-dimethyl-2-buten-1-yl, phenoxymethyl, chlorophenoxyethyl, methylthiomethyl, methylthioethyl, methylsulfinylmethyl, methylsulfonylethyl, ethylsulfonylpropyl, ethylthiomethyl, phenylthiomethyl, nitrophenylthiomethyl, chlorophenylthiomethyl, dimethylaminoethyl, diethylaminoethyl, acetylmethyl, propionylmethyl, pivaloylmethyl, phenacyl, nitrophenacyl, chlorophenacyl, bromophenacyl, methylphenacyl, methanesulfonylphenacyl, acetoxymethyl, propionyloxymethyl, butyryloxypropyl, methoxycarbonyloxyethyl, ethoxycarbonyloxyethyl, pivaloyloxymethyl, succiniminomethyl, phthaliminomethyl, cyanomethyl, 1,1-dimethylcyanomethyl, benzyl, chlorobenzyl, nitrobenzyl, methoxybenzyl, dimethoxybenzyl, dimethoxynitrobenzyl, trimethoxybenzyl, hydroxy-di-t-butylbenzyl, trichlorobenzyl, pentachlorobenzyl, phenethyl, benzhydryl, dimethoxybenzhydryl, α,α-dimethyldimethoxybenzyl, trityl, furylmethyl, quinolylmethyl, 1-oxidoquinolylmethyl, thienylmethyl, 9,10-dihydroanthryl, phenyl, tolyl, xylyl, indanyl, trichlorophenyl, pentachlorophenyl, nitrophenyl, dinitrophenyl, diazophenyl, phenylazophenyl, methanesulfonylphenyl, naphthyl, benzotriazolyl, trimethylsilyl, methoxydimethylsilyl, diethoxymethylsilyl, ethylenedioxymethylsilyl, trimethylstannyl, and triethylstannyl esters), acid halides (e.g. chloride and bromide), acid anhydrides (e.g. anhydrides with methoxyformic acid, cyclohexyloxyformic acid), amides (e.g. with ammonia and methylamine) and hydrazides (e.g. isopropylhydrazide, diisopropylhydrazide, and di-secondary butylhydrazide).

Particularly important protected carboxy are those inert in the reaction condition and removable without undesirable change in other parts of the molecule, exemplified by haloalkyl, acylalkyl, alkoxyalkyl, acyloxyalkyl, aralkyl esters, dialkylhydrazide, alkali metal salts, alkylamine salts, and like groups.

The lower alkyl and aryl for Q in Compounds IV

The lower alkyl for Q includes $C_1$ to $C_5$ alkyl e.g. methyl, ethyl, propyl, and isopropyl; and aryl for Q can be phenyl or optionally substituted phenyl e.g. tolyl, methoxyphenyl, chlorophenyl, and isopropylphenyl. Most preferable Q is hydrogen.

The nucleophilic group of Z in Compounds IV

Representatives of nucleophilic groups Z include halogen (e.g. chlorine, bromine, iodine), oxygen functions (e.g. alkoxy, aralkoxy, aryloxy, organic or inorganic acyloxy, hydroxy), sulfur functions (e.g. alkylthio, aralkylthio, arylthio, organic or inorganic acylthio, mercapto, sulfo, alkylsulfonyl), nitrogen functions (e.g. azido, aliphatic or aromatic amino or ammonio, amino, nitro, nitroso) and other nucleophiles. Among these, aryls can be phenyl, naphthyl, or heterocyclic aromatic group which can be substituted by a inert substituent. Preferable nucleophiles contain up to 10 carbon atoms.

Representatives of typical specific nucleophilic groups include fluorine, chlorine, bromine, iodine, hydroxy, methoxy, ethoxy, propoxy, isopropoxy, butoxy, acetoxy, propionyloxy, butyryloxy, isobutyryloxy, pivaloyloxy, cyclobutylcarboxy, carbamoyloxy, methylcarbamoyloxy, ethylcarbamoyloxy, chloroethylcarbamoyloxy, trichloroethoxycarbamoyloxy, dimethylcarbamoyloxy di-(methoxybenzyl)carbamoyloxy, phenylcarbamoyloxy, anisylcarbamoyloxy, sulfophenylcarbamoyloxy, carboxymethylphenylcarbamoyloxy, methanesulfonyloxy, sulfonyloxy, methanesulfinyloxy, benzyloxy, phenethyloxy, toluenesulfonyloxy, benzoyloxy, chlorobenzyloxy, tolylcarbonyloxy, cinnamoyloxy, hydroxycinnamoyloxy, sulfocinnamoyloxy, naphthoyloxy, tetrahydrofurylacetyloxy, methylthio, ethylthio, aminoethylthio, propylthio, dimethylpropylthio, isobutylthio, dithioacetyl, thiopropionylthio, propylthiocarbonylthio, xanthoyl, cyclopentyloxythiocarbonylthio, thiocarbamoylthio, dimethylthiocarbamoylthio, phenylthio, aminophenylthio, nitrophenylthio, benzylthio, tosylthio, furylthio, furylcarbonylthio, pyrrolidinylthio, pyrrolylthio, isoxazolylthio, isothiazolylthio, thiazolylthio, imidazolylthio, methylimidazolylthio, pyranylthio, pyridylthio, pyrimidylthio, methylpyrimidylthio, oxadiazolylthio, methyloxadiazolylthio, methyloxadiazolylthio, propyloxadiazolylthio, thiadiazolylthio, ethylthiadiazolylthio, ethylthiothiadiazolylthio, aminothiadiazolylthio, triazolylthio, cyanotriazolylthio, methyltriazolylthio, methoxytriazolylthio, tetrazolylthio, methyltetrazolylthio, indolylthio, benzoxazolylthio, benzothiazolylthio, methylamino, ethylamino, diethylamino, trimethylammonio, acetamido, chloroethylamino, ureido, thioacetamido, thiopropionamido, thiocarbamoylamino, methylureido, ethylthiocarbamoylamino, cyclohexylaminothiocarbonylamino, anilino, tolylamino, methylnitrophenylamino, thiobenzoylamino, naphthylamino, pyrrolidyl, methylpyrrolyl, pyridazinyl, triazinyl, pyridinium, chloropyridinium, methylpyridinium, nicotinium, dimethylpyridinium, quinolinium, trifluoromethylpyridinium, and carbamoylpyridinium.

Representative of specific compounds include the following compounds:

(1) Compounds of the formula:

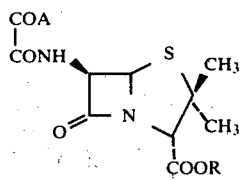

(2)

(wherein COA is lower alkoxycarbonyl or aralkyloxycarbonyl and R is lower alkyl or aralkyl)

More specific compounds (2) include those wherein (i) COA is methoxycarbonyl and R is benzyl,
(ii) COA is benzyloxycarbonyl and R is methyl, or
(iii) COA is methoxycarbonyl and R is diphenylmethyl;

(2) Compounds of the formula:

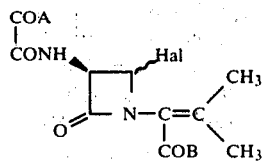

(3)

(wherein COA and COB each is lower alkoxycarbonyl or aralkoxycarbonyl and Hal is halogen)

More specific compounds (3) include those wherein (i) COA is methoxycarbonyl, COB is benzyloxycarbonyl, and Hal is chlorine;
(ii) COA is benzyloxycarbonyl, COB is methoxycarbonyl, and Hal is chlorine; or
(iii) COA is methoxycarbonyl, COB is diphenylmethoxycarbonyl and Hal is chlorine.

(3) Compounds of the formula:

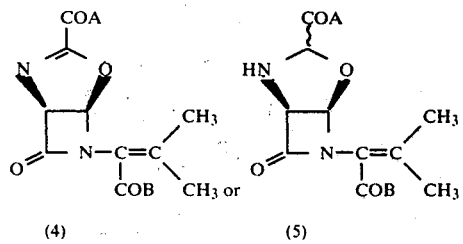

(4)  (5)

(wherein COA and COB each is lower alkoxycarbonyl or aralkoxycarbonyl)

More specific compounds (4) and (5) include those wherein (i) COA is methoxycarbonyl and COB is benzyloxycarbonyl,
(ii) COA is benzyloxycarbonyl and COB is methoxycarbonyl, or
(iii) COA is methoxycarbonyl and COB is diphenylmethoxycarbonyl.

(4) Compounds of the formula:

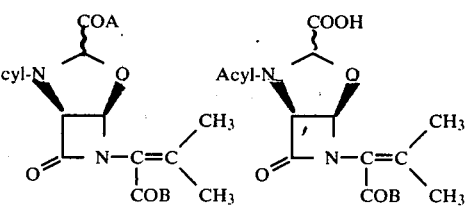

(6)  (7)

(8)  (9)

(wherein COA and COB each is lower alkoxycarbonyl or aralkoxycarbonyl;

Acyl is alkanoyl, aralkanoyl, aroyl, sulfonyl, or carbonic acyl;

Hal is halogen; and

Q is hydrogen, alkyl, or aryl)

More specific compounds (6) include those wherein (i) COA is methoxycarbonyl, COB is benzyloxycarbonyl, and Acyl is phenylacetyl, benzoyl, carbobenzoxy, or benzylsulfonyl;
(ii) COA is benzyloxycarbonyl, COB is methoxycarbonyl, and Acyl is phenylacetyl; or
(iii) COA is methoxycarbonyl, COB is diphenylmethoxycarbonyl, and Acyl is phenylacetyl.

More specific compounds (7) include those wherein (i) COB is benzyloxycarbonyl and Acyl is phenylacetyl, benzoyl, carbobenzoxy, or benzylsulfonyl;
(ii) COB is methoxycarbonyl and Acyl is phenylacetyl; or
(iii) COB is diphenylmethoxycarbonyl and Acyl is phenylacetyl.

More specific compounds (8) include those wherein (i) COB is benzyloxycarbonyl, Acyl is phenylacetyl, benzoyl, carbobenzoxy, or benzylsulfonyl, and Hal is chlorine; or
(ii) COB is methoxycarbonyl, Acyl is phenylacetyl, and Hal is chlorine;
(iii) COB is diphenylmethoxycarbonyl, Acyl is phenylacetyl, and Hal is chlorine.

More specific compounds (9) include those wherein (i) COB is benzyloxycarbonyl, Acyl is phenylacetyl, benzoyl, carbobenzoxy, or benzylsulfonyl, and Q is hydrogen;
(ii) COB is methoxycarbonyl, Acyl is phenylacetyl, and Q is hydrogen; or
(iii) COB is diphenylmethoxycarbonyl, Acyl is phenylacetyl, and Q is hydrogen.

(5) Compounds of the formula:

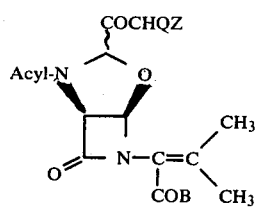

(wherein COB is lower alkoxycarbonyl or aralkoxycarbonyl;
Acyl is alkanoyl, aralkanoyl, aroyl, sulfonyl, or carbonic acyl;
Q is hydrogen, lower alkyl, or aryl; and
Z is hydrogen or nucleophilic group)

More specific compounds (10) include those wherein
(i) COB, Acyl, and Q are defined above; and Z is acetoxy or chlorine;
(ii) COB, Acyl, and Q are as defined above, and Z is hydrogen;
(iii) COB, Acyl and Z are as defined above, and Q is hydrogen;
(iv) COB is benzyloxycarbonyl, Acyl is phenylacetyl, benzoyl, carbobenzoxy, or benzylsulfonyl, and Z is hydrogen, chlorine, or acetoxy; or
(v) COB is methoxycarbonyl, or diphenylmethoxycarbonyl, Acyl is phenylacetyl, and Z is hydrogen or chlorine.

USE OF THE COMPOUNDS

The Compounds IV (where COX is —COCHQZ in which Q and Z are as defined above) were found to be reduced with e.g. aluminium amalgam and acetic acid to give Compounds 11 according to Reaction 13 as described latter.

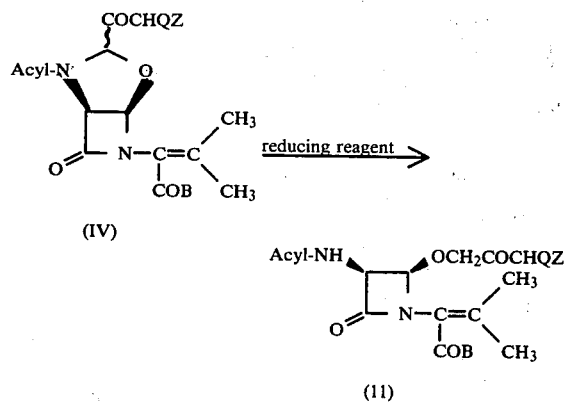

(wherein Acyl, COB, Q and Z are as defined above)

The compounds (11) can be used for synthesizing so-called antibacterial 1-oxacephalosporins, for example, according to the process illustrated in the following chart, as is disclosed in British Patent Application No. 46759 filed Nov. 12, 1975 and No. 33,109 filed Aug. 9, 1976:

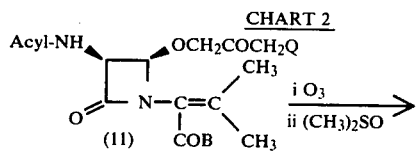

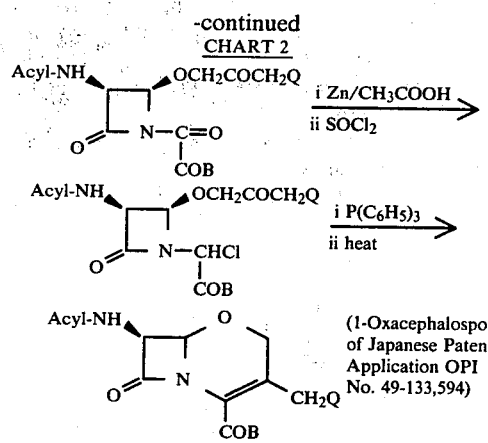

(wherein COB, Q, and X are as defined above)

Compounds (I) through (IV) can also be useful as intermediates for preparing other useful compounds within or beyond the scope of the compounds given hereinabove according to the given or known methods.

MERITS OF THIS INVENTION

Compounds (11) have been prepared by us from e.g. known 6-tritylaminopenicillanic acid according to the following reaction sequence of Chart 3, but the reaction (iv) usually takes place from the both of α and β sides at a ratio close to 1:1. Therefore, overall yield of the final products cannot theoretically exceed 50%, and usually less than 20%. The process of this invention, has no neck of the process, and generally the overall yield is about (30% to 50%) accompanied by scarce of uneasily separable by-products.

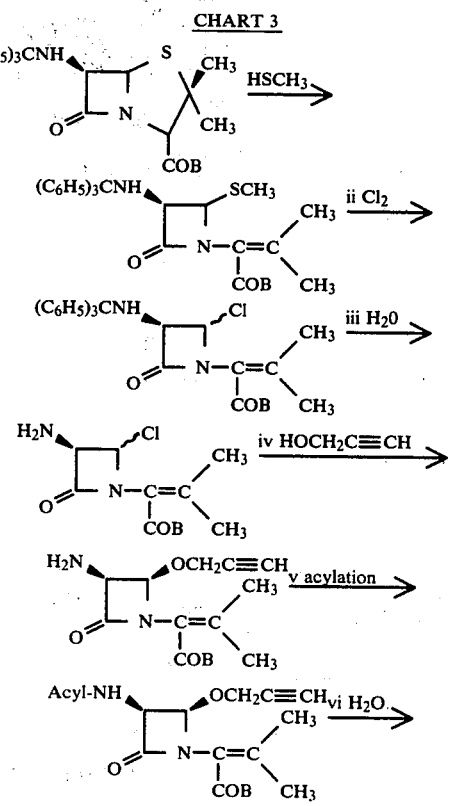

-continued
CHART 3

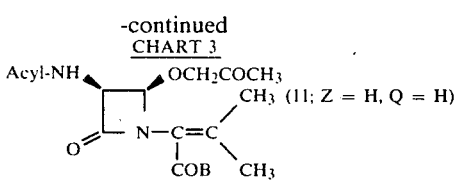

Compounds (I) through (IV) are useful as indispensable intermediates for the processes of this invention.

PROCESSES

The compounds of this invention can be prepared by the following reactions from known compounds.

(Reaction 1)

A reaction of 6-aminopenicillanic acid lower alkyl or aralkyl ester (1) with an oxalic acids (i) or reactive derivatives thereof gives Oxalylaminopenicillanate (2) according to the process of the following reaction scheme:

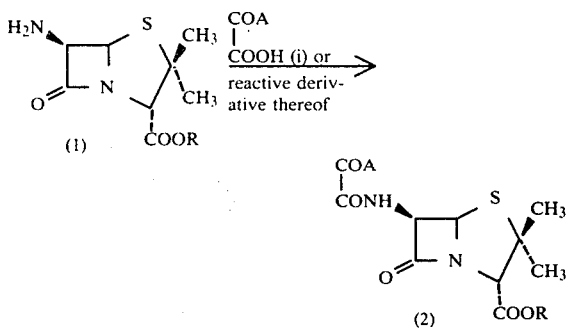

(wherein COA is carboxy or protected carboxy and R is lower alkyl or aralkyl)

The reactive derivatives of the oxalic acids (i) include the following reagents:

(1) the free acid—in the presence of a condensing reagent such as carbodiimides (e.g. N,N'-diethylcarbodiimide, N,N'-dipropylcarbodiimide, N,N'-diisopropylcarbodiimide, N,N'-dicyclohexylcarbodiimide, and N-ethyl-N'-3-dimethylaminopropylcarbodiimide), carbonyl compounds (e.g. carbonyldiimidazole), isoxazolinium salts (e.g. N-ethyl-5-phenylisoxazolinium-3'-sulfonate and N-t-butyl-5-methylisoxazolinium perchlorate), acylamino compounds (e.g. 2-ethoxy-1-ethoxycarbonyl-1,2-dihydroquinoline), or like condensing reagents—utilizable in a nonprotic solvent (especially halohydrocarbon, nitrile, ether, and amide solvents or mixtures thereof) at about −30° C. to +100° C. (preferably from −10° C. to 50° C.) for 10 minutes to 24 hours, and preferably at a molar ratio of 1 to 2 of the free acid and 1 to 2 of the condensing reagent against 6-aminopenicillanic acid lower alkyl or aralkyl ester (1).

(2) an acid anhydride—including symmetrical anhydrides; mixed anhydrides with a mineral acid e.g. a half ester of carbonic acid e.g. lower alkyl (e.g. methyl, ethyl, propyl, isopropyl, butyl, isobutyl, sec-butyl, pentyl, cyclopropylmethyl, cyclopentyl, and cyclohexyl) half esters of carbonic acid; mixed anhydrides with alkanoic acids (e.g. formic acid, acetic acid, pivalic acid, trifluoroacetic acid, and trichloroacetic acid), mixed anhydrides with sulfonic acid (e.g. toluene-p-sulfonic acid), and intramolecular anhydrides (e.g. ketene and isocyanate)—utilizable preferably in the presence of an acid acceptor including inorganic base [e.g. hydroxides, carbonates, or bicarbonates of alkali metal (e.g. sodium and potassium), or alkaline earth metal (e.g. magnesium and calcium)]; alkaline earth metal oxides; organic bases including tertiary amines (e.g. trimethylamine, triethylamine, dimethylethylamine, propyldimethylamine, tripropylamine, N-methylmorpholine, and dimethylaniline), and aromatic bases (e.g. pyridine, quinoline, collidine, and picoline)]; oxiranes (e.g. ethylene oxide, propylene oxide, and cyclohexene oxide)—in a nonprotic solvent (especially halohydrocarbon, nitrile, ether, and amide solvents or mixtures thereof) at about −30° C. to +100° C. (preferably from −10° C. to 50° C.) for 10 minutes to 24 hours, and preferably at a molar ratio of 1 to 2 of the anhydride and 1 to 10 of the acid acceptor against the 6-aminopenicillanic acid lower alkyl or aralkyl ester (1);

(3) an acid cyanide, acid azide, or acid halide (e.g. chloride and bromide)—preferably in the presence of an acid acceptor mentioned for the acid anhydrides—in a solvent (especially halohydrocarbon, nitrile, ether, ketone, water, and amide solvents or mixtures thereof) at about −30° C. to +100° C. (preferably from −10° C. to 50° C.) for 10 minutes to 6 hours—and preferably at a molar ratio of 1 to 2 of the reactive derivatives and 1 to 10 of the acid acceptor against the 6-aminopenicillanic acid lower alkyl or aralkyl ester (1);

(4) a reactive ester—including enol esters (e.g. vinyl and isopropenyl esters), aryl esters (e.g. chlorophenyl, bromophenyl, nitrophenyl, dinitrophenyl, nitrochlorophenyl, and pentachlorophenyl esters), heterocyclic aryl esters (e.g. benzotriazolyl esters), and diacylamino esters (e.g. succinimido and phthalimido esters);

(5) a reactive amide—including amide with an aromatic amine (e.g. imidazole, triazole, and 2-ethoxy-1,2-dihydroquinoline), and N-substituted-N,N-diacylamines (e.g. diacylaniline);

(6) a formimino compound including N,N-dimethyliminomethyl derivative of the oxalic acid (i): and other reactive derivatives. The reactive ester, reactive amide, and formimino compounds can be used in a non-protic solvent (especially halohydrocarbon, ether, ketone, amide, and ester solvents or mixtures thereof) by merely mixing with the reagents at a molar ratio of 1 or more against the starting material (1) at about −30° C. to +100° C. for 30 minutes to 6 hours.

The starting material (1) may be subjected to this acylation after protecting or activating the amino group by conventional groups e.g. silyl (e.g. trimethylsilyl and dimethylmethoxysilyl), stannyl (e.g. trimethylstannyl), 1-haloalkylidene, 1-haloaralkylidene, 1-alkoxyalkylidene, 1-alkoxyaralkylidene, carbonyl, sulfenyl, or readily removable acyls, and the groups can be removed after the reaction to give the objective compounds.

The group COA and COOR are usually replaced by carboxy separately at a desirable stage of synthesis of final objective compounds. The structure of the two groups can be varied widely so far as they are stable to the reaction and removable at a required stage, as is described above.

When R is hydrogen, the reaction has been described in Japanese Patent Application Publication No. 39-6678.

(Reaction 2)

The Oxalylaminopenicillanate (2) can be treated with a halogenating reagent to give a haloazetidinone (3) according to the following reaction scheme:

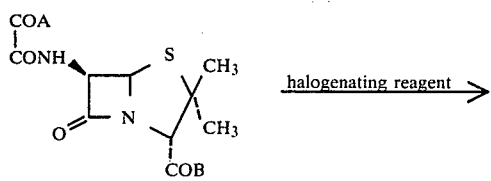

(2)

halogenating reagent →

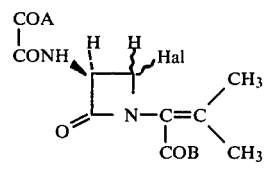

(3)

(wherein COA and COB each is carboxy or protected carboxy; and Hal is halogen)

The halogenating reagent include molecular halogen (e.g. chlorine and bromine), hypohalogenous acid source (e.g. hypohalides, N-haloamides e.g. N-chlorosuccinimide, N-bromosuccinimide, N-iodosuccinimide, N-chlorophthalimide, N-bromophthalimide, N-chloroacetamide, N-bromoacetamide, and Chloramines B and T); iodobenzene dihalodes, sulfuryl halide; as a solution in non-polar solvent (e.g. halohydrocarbon, ether, ester solvents or mixtures thereof).

This reaction applied to 6β-phthalimidopenicillanic acid esters has been reported in Journal of the American Chemical Society, 93, 6267 (1971), 94, 7590 (1972); Canadian Journal of Chemistry, 50, 2894, 2898, 2902 (1973), 53, 497 (1975); Journal of Chemical Society 1975, 1932, but not known in the cases of oxalylaminopenicillanic acid derivatives.

Haloazetidinone (3) may also be prepared from α-[3β-(oxalylamino)-4β-alkylthio-2-oxoazetidin-1-yl]-α-isopropylideneacetic acid or derivatives thereof on the action of said halogenating reagents. For example, a solution of molecular halogen dissolved in carbon tetrachloride is added to a methylene chloride solution of the 4β-alkylthio compounds under ice cooling, and the mixture is stirred to give the haloazetidinone (3) in good yield.

In a preferable example, Oxalylaminopenicillanate (2) is stirred with 1 to 5 mole equivalents of chlorine in a nonprotic inert solvent (especially halohydrocarbon solvents) at −50° C. to +10° C. (especially at −20° C. to 0° C.) for 10 to 60 minutes to give Haloazetidinone (3) in 60 to 90% yield.

(Reaction 3)

The Haloazetidinone (3) can be treated with a dehydrohalogenating reagent to give a Oxazolinoazetidinone (4) according to the following reaction scheme:

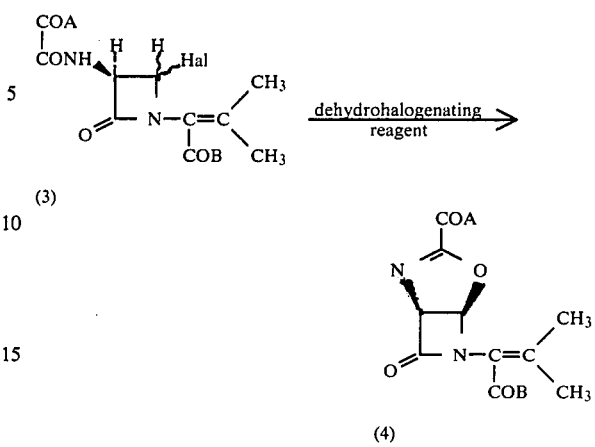

(wherein COA and COB each is carboxy or protected carboxy and Hal is halogen)

Representatives of the dehydrohalogenating reagents are salts of a metal having an affinity to halogen ion (e.g. silver, zinc, tin, aluminum, titanium, iron, alkali metal, alkaline earth metal in forms of mineral acid salts, alkanoate salts, haloalkanoate salts, sulfonate salts, Lewis acid salts, and like salts, especially those being lipophilic are suitable for the reaction. Preferable dehydrohalogenating reagents are zinc chloride, titanium chloride, aluminium chloride, ferrous chloride, ferric chloride, stannous chloride, zinc sulfate, ferric nitrate, titanium bromide, silver tetrafluoroborate, sodium hydrogencarbonate, potassium hydrogencarbonate, calcium carbonate, sodium carbonate, potassium carbonate, zinc acetate, and like salts.

Sometimes, the dehydrohalogenation also takes place by the action of basic compounds (e.g. lower alkylamine, N-methylmorpholine, N-methylpiperidine, pyridine, sodium carbonate, and calcium oxide) or adsorbents (e.g. silica gel and alumina), or by merely refluxing under heating in a solvent in moderate yield of the product (4). These dehydrohalogenating reagents are also included in the scope of the reagents for this Reaction 3.

Compounds (4) substituted by a phenoxymethyl or benzyl in place of COA have been described in some literatures (Journal of Chemical Society, Chem. Comm. 1972, 229; Canadian Journal of Chemistry, 50, 2902 (1972); Journal of Chemical Society, 1975, 883 and 1932; Canadian Journal of Chemistry, 53, 497 (1975)). Particularly, the oxazolinoazetidinone (4) have been prepared by Wolfe et al. from a compound analogous to those of the formula (3) by shaking or refluxing in an organic solvent with an aqueous solution of sodium hydrogencarbonate. It has been confirmed that this reaction is also applicable to the present invention, that is, the location of a carbonyl group adjacent to the amidocarbonyl did not interfere with the proceeding of the reaction.

Both of isomers of the 4α- and 4β-halogenated starting compounds give the same Oxazolinoazetidinone (4) in approximately the same yield.

In a representative example, Haloazetidinone (3) is dissolved in an inert solvent (e.g. ether, ketone, and amide solvent) at a temperature of −50° C. to +100° C. (especially −30° C. to 30° C.), mixed with the dehydrohalogenating reagent (especially silver tetrafluoroborate, zinc chloride, and stannous chloride), if required in the presence of a base (e.g. methylmorpholine), and let react for 10 minutes to 12 hours (especially 15 minutes to 60 minutes) to give Oxazolinoazetidinone (4) in 80 to 99% yield.

(Reaction 4)

The Oxazolinoazetidinone (4) can be treated with a reducing reagent to give an Oxazolidine (5) according to the following reaction scheme:

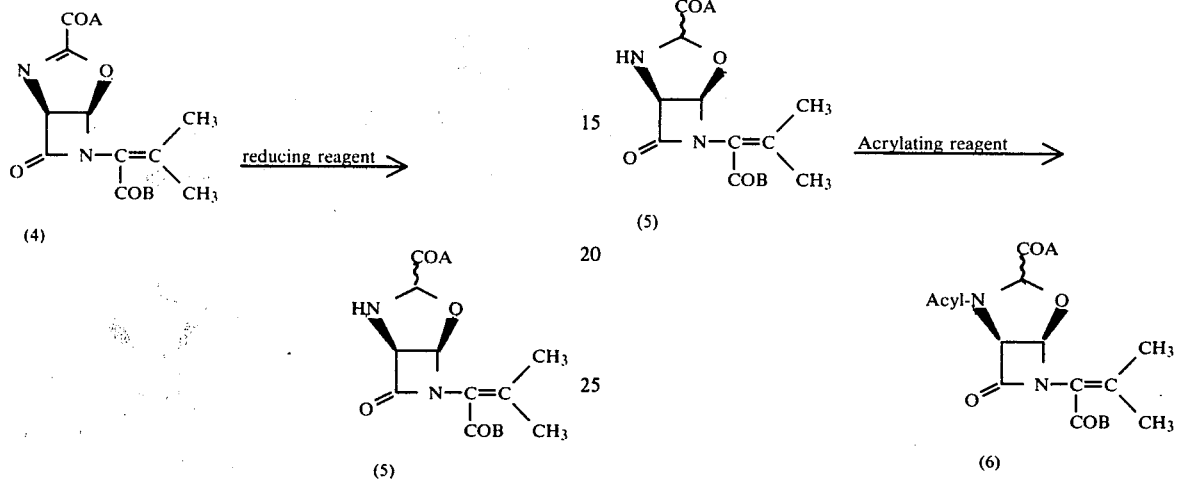

(wherein COA and COB each is carboxy or protected carboxy)

Representative reducing reagents are metals including alkali metal (e.g. sodium, potassium, and lithium), alkaline earth metal (e.g. magnesium and calcium), metals of Group III in the periodical table (e.g. boron and aluminium), and transition metals (e.g. iron, cobalt, and nickel) or amalgams thereof in the presence of a proton source (e.g. water, alcohol, acid, and alkali); borane derivatives (e.g. pyridine borane); complexes of aluminium hydride or boron hydride with metal hydride (e.g. lithium aluminium hydride, potassium aluminium hydride, sodium methoxyaluminium hydride, lithium t-butylaluminium hydride, and sodium borohydride); salts, carbonyl compounds or organometallic compounds involving multivalence metal (e.g. iron, nickel, chromium, and cobalt) at low valence stage.; hydride donating reducing reagents, electrolytic reduction; and other reducing reagents and methods.

Most preferable reducing reagents for this reaction are zinc and mineral acid, aluminium amalgam and water, sodium cyanoborohydride, and like reducing reagents.

This type of the reaction is known on 3-substituted-alkyl-thiazolinoazetidine compounds (Japanese Patent Application OPI No. 47-17792; U.S. Pat. No. 3,681,380), but not in the case where COA is carboxy or protected carboxy.

The present inventors have discovered that the reduction of carbonyl group bound directly to the 3-position is preceded by reduction of the oxazoline ring, and when the degree of carbonyl unsaturation is decreased in forms of carboxy, esters, amides, salts, and the like, the reduction proceeds more easily. The present process is based on this discovery.

In a representative example, the Oxazolinoazetidinone (4) is dissolved in an inert solvent (e.g. ether, ester, and alcohol solvents), mixed with water and aluminium amalgam at 0° C. to 50° C. for 30 minutes to 5 hours (preferably 1 to 3 hours) to give the Oxazolidine (5) in high yield.

(Reaction 5)

The Oxazolidine (5) can be acylated with an acylating reagent to give N-Acyloxazolidine (6) according to the following reaction scheme:

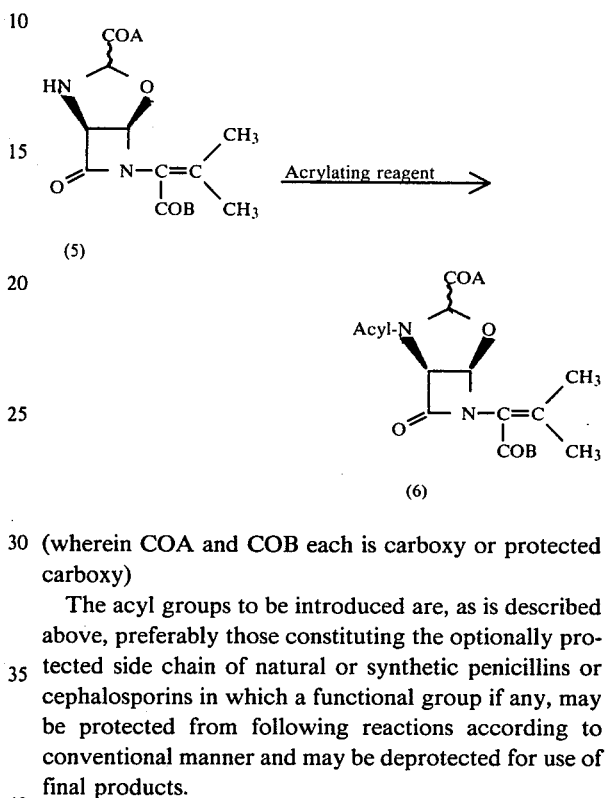

(wherein COA and COB each is carboxy or protected carboxy)

The acyl groups to be introduced are, as is described above, preferably those constituting the optionally protected side chain of natural or synthetic penicillins or cephalosporins in which a functional group if any, may be protected from following reactions according to conventional manner and may be deprotected for use of final products.

The acylating reagent is a reactive derivative of an acid having the desired acyl group. The reaction is easily carried out by applying the reaction conditions and reactive derivatives similar to those described above in relation to Reaction 1 for the preparation of the Oxalylaminopenicillins (2).

Particularly preferred acyl groups are those increasing selectivity and reactivity of the subsequent reactions and readily removable at a required stage of synthesis if desired.

In a preferable example, 1 mole equivalent of an Oxazolidine (5) is treated with 1 to 2 mole equivalents of an acid chloride of phenylacetic acid, benzoyl chloride, benzylsulfonyl chloride, or benzyl chloroformate, in the presence of 1 to 2 mole equivalents of an organic base (e.g. triethylamine and pyridine) at −50° C. to 30° C. (especially from −30° C. to 10° C.) for 10 minutes to 5 hours (especially from 30 minutes to 2 hours) in an inert solvent (especially halohydrocarbon, ether, ketone, amide, and ester solvents).

(Reaction 6)

The N-Acyloxazolidine (6) can be deprotected at COA group selectively to give Free acid (7) according to the following reaction scheme:

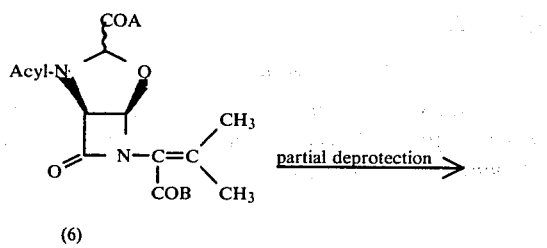

(6)

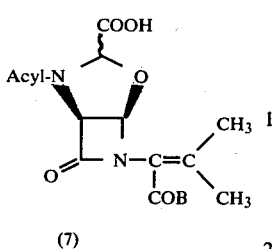

(7)

(wherein COA and COB each is carboxy or protected carboxy)

The N-acyloxazolidine (6) is much more stable to various reaction conditions than those having penam or cephem structure, and it tolerates such deprotection conditions as hydrolysis including hydrolysis even with mineral acids (e.g. hydrochloric acid, sulfuric acid, phosphoric acid, nitric acid, perchloric acid) and alkali metal hydroxide (e.g. sodium hydroxide, potassium hydroxide), solvolysis (with e.g. trifluoroacetic acid and cation scavenger; hydrogen bromide and acetic acid), hydrogenolysis over catalysts (e.g. palladium, platinum, and nickel), reduction (with e.g. sodium borohydride, lithium aluminum hydride, sodium borohydride), oxidation (with e.g. chromium trioxide and manganese oxides), dealkylation (nucleophilic dealkylation e.g. with lithium iodide, lithium thiophenoxide, and lithium t-butylmercaptide), anion or cation exchange reaction, and other conventional reaction conditions. These reactions are applicable to the said partial deprotection.

As it is necessary to make the 3-carboxy group free while α-carboxy being protected, the protecting groups in COA and COB in N-acyloxazolidine (6) are different each other, and deprotected by different means or conditions. It is preferable therefor to select such COA and COB at the stage of introduction of said protected carboxy groups in former reactions. Such procedure is conventional in the synthetic chemistry.

In a preferable example, 1 mole of N-Acyloxazolidine (6) is treated with diluted sodium hydroxide in water (e.g. from 0.1 to 10) in a solution of an inert solvent (e.g. ether or ketone solvent, or mixtures thereof), at −20° C. to 100° C. (especially from −10° C. to 50° C.) for 30 minutes to 5 hours to give the Free acid (7) up to 95% yield.

In another preferable example, when COA is benzyloxycarbonyl, the N-Acyloxazolidine (6) is hydrogenated over palladium carbon in tetrahydrofuran at room temperature until the consumption of hydrogen ceases to give the Free acid (7).

In other preferable example, when COA is diphenylmethoxycarbonyl, the N-Acyloxazolidine (6) is dissolved in trifluoroacetic acid in the presence of anisole at room temperature, and the solution is evaporated after 30 minutes to give the Free acid (7).

Reactions from 7 to 10 are conventional diazoketone synthesis for preparing a Ketone (10) from a Free acid (7) in 85 to 90% over-all yield.

(Reaction 7)

The Free acid (7) can be treated with a halogenating reagent for preparing acid halides to give a Acid halide (8) according to the following reaction scheme:

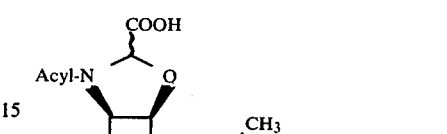

(7)

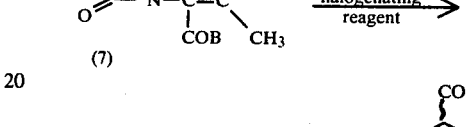

(7)

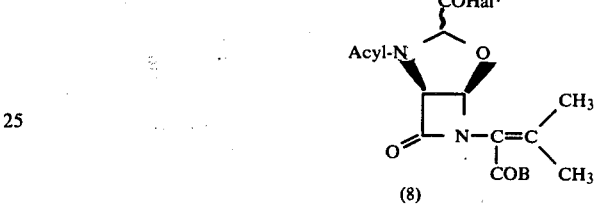

(8)

(wherein COB is carboxy or protected carboxy and Hal$^1$ is halogen)

The halogenating reagents for this reaction 7 are those which are usually used in preparing acid halides from carboxylic acids; particularly preferable ones are Vilsmeier type reagents (e.g. dimethylformamide and phosgene or thionyl chloride), thionyl halides, phosphorus pentahalides, phosphorus oxyhalides, oxalyl halides, and triphenylphosphine in carbon tetrachloride).

The Free acid (7) may first be converted into an alkali metal salts prior to the action of the halogenating reagent.

Preferable halogens for the halogenating reagent or Hal$^1$ are chlorine or bromime.

In a preferable example, the Free acid (7) is treated with oxalyl chloride, thionyl chloride, or phosphorus pentachloride in an inert solvent (especially hydrocarbon, halohydrocarbon, or amide solvents and mixtures thereof) at 0° C. to 100° C. for 10 minutes to 5 hours to give the Acid halide (8).

(Reaction 8)

The Acid halide (8) can be treated with a diazo compound (ii) to give a Diazoketone (9) according to the following reaction scheme:

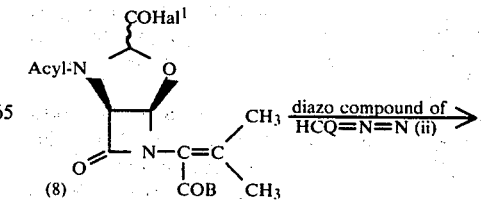

(8)

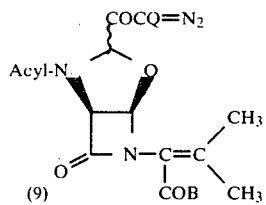

(wherein COB is carboxy or protected carboxy;
Hal[1] is halogen; and
Q is hydrogen, lower alkyl or aryl)

The diazocompound (ii) is a diazoalkane or diazoaralkane. The reaction proceeds well in a solvent in which both of reactant and reagent are brought to contact according to conventional manner preferably at $-10°$ C. to 50° C. for 10 minutes to 5 hours to give the Diazoketone (9) in high yield.

The product may be isolated in a conventional manner without decomposition or for the further synthesis, it may be subjected to the following reaction 9 without isolation.

In a preferable example, the Acid halide (8) is dissolved in an inert solvent (especially ether and halohydrocarbon solvents or mixtures thereof), mixed with a solution of diazomethane at 0° C. to 30° C. for 20 minutes to 2 hours to give the Diazoketone (9) in high yield.

(Reaction 9)

The Diazoketone (9) can be treated with a nucleophilic compound (iii) to give an optionally substituted methylketone (10) according to the following reaction scheme:

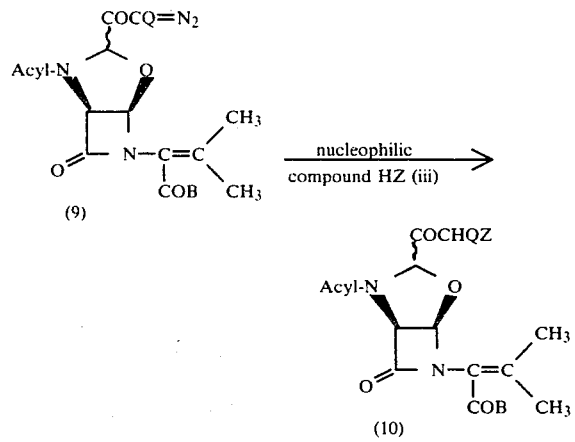

(wherein COB is carboxy or protected carboxy;
Q is hydrogen, alkyl or aryl; and
Z is hydrogen or nucleophilic group)

The nucleophilic compound (iii) represented by the formula HZ is that having the Z group to be introduced, and are exemplified by a hydrogen halide, hydrogen azide, alcohol, phenol, organic acid, inorganic acid, water, mercaptane, thiophenol, thiol acid, hydrogen sulfide, amine, or the other nucleophilic compounds represented by the formula HZ in which Z is as defined above for the Compounds IV.

A compound forming a nucleophilic compound (iii) under the reaction condition is also included in the definition of the nucleophilic compounds for this reaction, as a reactive derivative.

In a preferable case, a Diazoketone (9) is dissolved in an inert solvent (especially ether, ketone, halohydrocarbon, or mixtures thereof) and mixed with ether saturated with hydrogen chloride at $-10°$ C. to 50° C. for 15 minutes to 5 hours to give a chloromethylketone (10, Z=Cl).

In another example, a Diazoketone (9) is dissolved in acetic acid containing boron trifluoride etherate to give an acetoxymethylketone (10, Z=—OCOCH$_3$).

(Reaction 10)

The Haloketone (10; Z=Hal[2]) can be treated with a reducing reagent to give a ketone (10; Z=H) according to the following reaction scheme:

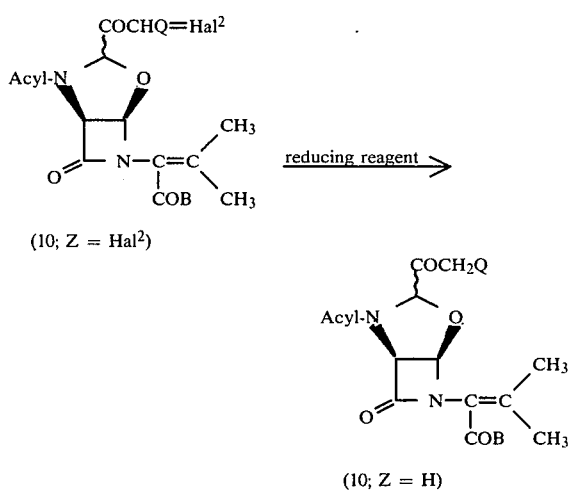

(wherein COB is carboxy or protected carboxy;
Hal[2] is halogen; and
Q is hydrogen, lower alkyl, or aryl)

The preferable reducing reagents include a combination of reducing metal (e.g. zinc, iron, tin, and aluminium), or their amalgams and proton donor (e.g. acids, alcohols, and water); catalytic hydrogenation over a catalyst (e.g. palladium, platinum, and nickel), electrolytic reaction, and reduction with hydrides (e.g. sodium borohydride, potassium borohydride, zinc borohydride, and lithium methoxyaluminum hydride). The reduction can also be carried out by the treatment of the Haloketone (10; Z=Hal[2]) with an alkali metal iodide, hydrogen iodide, or the like, followed, by, if required by reduction.

The reduction carried out under more drastic condition than those specified above sometimes gives Compounds (11) as a result of accompanying Reaction 13.

In a preferable example of Reaction 10, a Haloketone (10; Z=Hal[2]) is dissolved in acetic acid and stirred with zinc powder at room temperature for 30 minutes to 2 hours yielding the Ketone (11) in high yield.

(Reaction 11)

The N-Acyloxazolidine (7) can be treated with an organometallic compound (iv) to give Ketone (10; Z=H) according to the following reaction scheme:

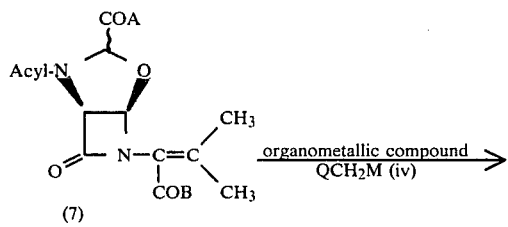

(7)

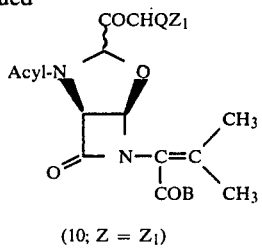

(10; Z = Z₁)

(wherein COB is carboxy or protected carboxy;

Q is hydrogen, lower alkyl or aralkyl;

$Z_0$ is the starting nucleophilic group; and $Z_1$ is the introduced nucleophilic group)

This reaction can be utilized for introduction of Z group in Compound (10) suitable for the purpose of the subsequent reactions or the use of the final products. For example, when the starting $Z_0$ is a halogen, the Compound (10) is treated with an alkali metal alkanoate or alkali metal heterocyclic mercaptide to give the corresponding compounds where Z is an alkanoyloxy or heterocyclic thio group.

(Reaction 13)

The optionally substituted ketone (10) can be treated with a reducing reagent to give an Acetonylazetidinone (11) according to the following reaction scheme:

(10; Z = H)

(wherein COA and COB each is carboxy or protected carboxy;

Q is hydrogen, lower alkyl or aralkyl; and

M is a monovalent metal or monohalodivalent metal or a half of divalent metal)

The organometallic compound (iv) is that capable of introducing a lower alkyl or aralkyl into a carboxy or protected carboxy to give a methylketone derivative. Representatives of the reagent (iv) include LiCu(CH₂Q)₂, QCH₂MgHal:CuHal, Cd(CH₂Q)₂, CH₃SOCHQNa, and like organometallic reagents for introducing QCH₂-group.

These organometallic reagents are brought to contact with an N-Acyloxazolidine (7) in a nonprotic solvent (especially hydrocarbon or their solvent or mixture thereof) under exclusion of moisture, if required in the presence of amine, to give objective Ketone (10; Z=H) in high yield.

The reaction may be classified into one of Grignard reaction, Blaise reaction, Corey reaction, or like reactions for ketone synthesis.

This route is more efficient than said Diazoketone synthesis described above (Reactions 7 through 11) as the process is simple and high yield.

(Reaction 12)

Compound (10) having Z being a nucleophilic group, can be subjected to exchange reaction with other type of nucleophilic reagent to give a Compound (10) where Z is more strong nucleophile than that of the starting material;

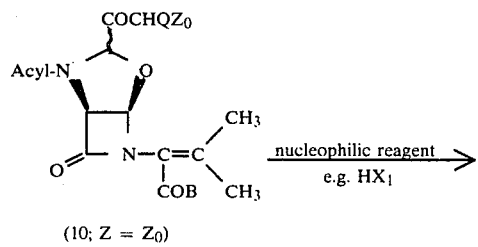

(10; Z = Z₀)

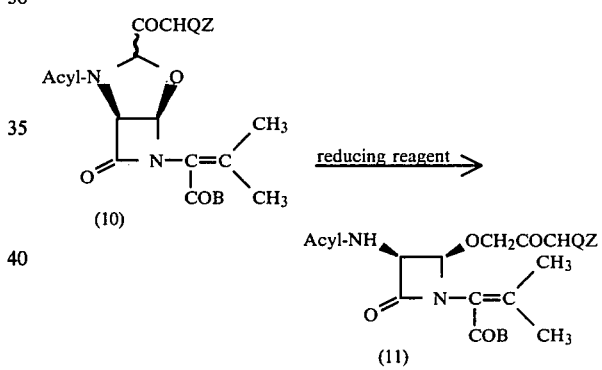

(wherein COB is carboxy or protected carboxy;

Q is hydrogen, lower alkyl or aryl; and

Z is hydrogen or nucleophilic group)

All of the reducing reagents which effectively cleave the oxazolidine ring without reduction of the carbonyl group attached to the 3-position may be utilized in this reduction step. This is a novel reaction never described in the chemistry of carbonyloxazolidines.

For example, the reduction can be carried out under the action of a reducing metal (e.g. zinc, iron, tin, magnesium, aluminium, and titanium) with a proton donor (including a hydrogen halide e.g. hydrogen chloride, hydrogen bromide, ammonium halide, ammonium chloride, ammonium bromide, sulfonic acid e.g. toluene-p-sulfonic acid, benzenesulfonic acid, methanesulfonic acid, mineral acids e.g. sulfuric acid, phosphoric acid, and nitric acid, acetic acid, trichloroacetic acid, and trifluoroacetic acid), in a solvent such as ether, amide, ester, alcohol, carboxylic acid solvents, or mixtures thereof. The addition of water sometimes promotes this reaction. Solvent such as hydrocarbons, esters, or halohydrocarbons may be used in order to dissolve the starting material.

Besides, organometallic reducing reagents of polyvalent metals (e.g. iron, cobalt, nickel) chromous salts, or electrolytic reduction may also be used for the reducing reagent specified above, which are included in the reaction of this step.

When the group Z is a readily reducible nucleophilic group, the group Z of a part of the product may be different from that of the starting material and probably Z is reduced Z or hydrogen.

In order to avoid such reductive change of Z group, it is appropriate to select suitable reducing reagents and reaction conditions according to conventional methods.

Consecutive application of the aforementioned processes starting from 6-aminopenicillanic acid down to Compound (11) gives those wherein the substituents at the 4-position of azetidine structure have single configuration. According to the prior art processes, the reaction gives a mixture of stereoisomers (epimers) at the position 4; since the epimers are closely resemble each other in their property, a special technique for separation such as precisious chromatograph is required. The processes of this invention does not require such troublesome procedures.

Each reaction as mentioned above may preferably be carried out in a solvent. The solvent may be selected according to the starting materials, reagents, reaction temperature, reaction time, the scale of the reaction, and other reaction conditions, and belong to conventional solvents including hydrocarbon (e.g. pentane, hexane, petroleum ether, cyclohexane, cycloheptane, isooctane, benzene, toluene, xylene, and cyclohexane), halohydrocarbon (e.g. dichloromethane, chloroform, trichloroethane, pentachloroethane, chlorobenzene, dichlorobenzene, and fluorobenzene), ether (e.g. diethyl ether, methyl isobutyl ether, dioxane, tetrahydrofuran, ethylene glycol diethyl ether, and anisole), ester (e.g. methyl acetate, ethyl acetate, butyl acetate, methyl benzoate, and dimethyl phthalate), ketone (e.g. acetone, methyl ethyl ketone, cyclohexanone, acetophenone, and benzophenone), nitrohydrocarbon (e.g. nitromethane, nitroethane, nitrobenzene, nitrotoluene, and nitroxylene), water, alcohol (e.g. methanol, ethanol, propanol, butanol, isobutanol, pentanol, cyclohexanol, cyclohexylmethanol, and octanol), nitrile (e.g. acetonitrile, propionitrile, and benzonitrile), and amide (e.g. formamide, acetamido, dimethylformamide, dimethylacetamide, benzamide, dimethylbenzamide, and benzoylmorpholine), solvents, and like solvents for chemical reactions.

The products in each step may be separated from the reaction mixture containing the unreacted starting materials, unreacted reagents, by-products, solvents, by conventional methods e.g. extraction, filtration, drying, concentration, adsorption, crystallization, chromatography, and like manners, and purified in conventional methods e.g. recrystallization, reprecipitation, chromatography, counter-current distribution, and like methods.

The following examples are provided to illustrate this invention in detail. The elemental analyses and physical constants of the products in each example are consistent with the given structures.

I INTRODUCTION OF OXALYL

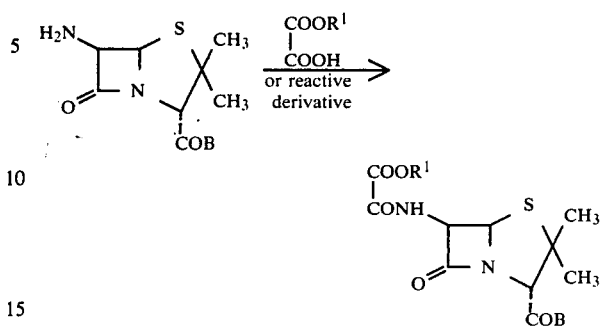

Example I-1 ($R^1$=—$CH_3$, COB=—$COOCH_2Ph$)

To a suspension of 80 g of benzyl 6-aminopenicillanate p-toluenesulfonate in 680 ml of tetrahydrofuran is added 51.3 ml of triethylamine under ice cooling with stirring, and then dropwise added a solution of 18.3 ml of the acid chloride of monomethyl oxalate in 20 ml of tetrahydrofuran to the mixture over a period of 20 minutes. The mixture is stirred for 30 minutes under ice cooling, diluted with 800 ml of ice water and extracted with ethyl acetate. The extract is washed with 5% aqueous solution of sodium hydrogencarbonate, water and then brine, dried on sodium sulfate and concentrated under reduced pressure. The residue is recrystallized from a mixture of methylene chloride and ether to yield 60 g of benzyl 6β-methoxalylaminopenicillanate melting at 113°–114.5° C. in 91.3% yield.

IR: $\nu_{max}^{CHCl_3}$ 3395, 1790, 1745, 1718, 1518 cm$^{-1}$.

NMR: $\delta^{CDCl_3}$ 1.43s3H, 1.67s3H, 3.93s3H, 4.55s1H, 5.25s2H, 5.5-5.8m2H, 7.43s5H, 7.8brs1H.

$[\alpha]_D^{23}$ +116.8÷2.1° (c=1.002, CHCl$_3$).

Example I-2 ($R^1$=—$CH_2Ph$, COB=—$COOCH_3$)

To a solution of 2.30 g of methyl 6-aminopenicillanate and 1.90 g of monobenzyl oxalate in 46 ml of tetrahydrofuran is added 2.17 g of N,N'-dicyclohexylcarbodiimide under ice cooling, and the mixture stirred for 30 minutes. The resulting crystals are removed by filtration and the filtrate is concentrated under reduced pressure. The residue is purified by chromatography on 100 g of silica gel containing 10% water and eluted with benzene containing 10% ethyl acetate to yield 1.8 g of methyl 6β-phenylmethoxalylaminopenicillanate in 46% yield.

IR: $\nu_{max}^{CHCL_3}$ 3380, 1790, 1750, 1720 cm$^{-1}$.

NMR: $\epsilon^{CDCl_3}$ 1.48s3H, 1.65s3H, 3.75s3H, 4.50s1H, 5.27s2H, 5.50d (3.5 Hz)1H, 5.60q(3.5; 8 Hz)1H, 7.33s5H, 7.72d(8 Hz)1H.

Example I-3 ($R^1$=—$CH_2Ph$, COB=—$COOCH_3$)

To a suspension of 16 g of sodium monobenzyl oxalate in 160 ml of methylene chloride containing 0.5 ml of N,N-dimethylformamide is added 6 ml of oxalyl chloride under ice-cooling and the mixture stirred for 30 minutes to yield a solution of the acid chloride. This is dropwise added to a solution of 15 g of methyl 6-aminopenicillanate and 11 ml of triethylamine in 150 ml of methylene chloride under ice-cooling and the mixture stirred for 20 minutes, washed with water, dried on magnesium sulfate and concentrated under reduced pressure. The residue is purified by chromatography on 250 g of silica gel containing 10% water and eluted with benzene containing 10% ethyl acetate to yield 16.9 g of methyl 6β-phenylmethoxalylaminopenicillanate in 66% yield.

EXAMPLE I-4 ($R^1$=—$CH_3$, COB=—COOCHPh$_2$)

To a suspension of 60.54 g of diphenylmethyl 6-aminopencillanate p-toluenesulfonate in 400 ml of tetrahydrofuran, are added 33 ml of triethylamine, and then 15 g of the acid chloride of monomethyl oxalate under ice-cooling, and the mixture stirred for 20 minutes and concentrated under reduced pressure to yield the residue, which is dissolved in ethyl acetate, washed with water, dried on magnesium sulfate and concentrated under reduced pressure to yield 55.91 g of diphenylmethyl 6β-methoxalylaminopenicillanate as crude product in 109.4% yield.

NMR: $\delta^{CDCl_3}$ 1.30s3H, 1.67s3H, 3.97s3H, 4.63s1H, 5.62d(3.5 Hz)1H, 5.73q(3.5; 8 Hz)1H, 7.03s1H, 7.43s10H, 7.83d(8 Hz)1H.

II. CLEAVAGE OF PENAM RING

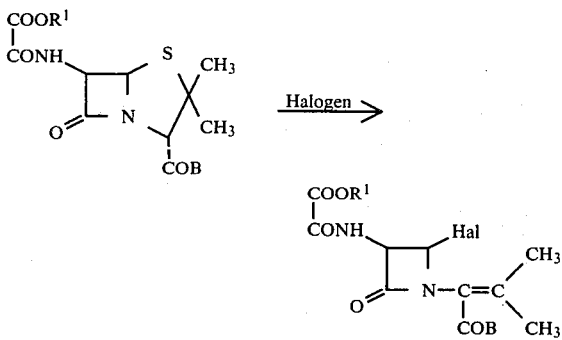

EXAMPLE II-1 ($R^1$=$CH_3$, COB=—COOCH$_2$Ph, Hal=Cl)

To a solution of 57.3 g of benzyl 6β-methoxalylaminopenicillanate dissolved in a mixture of 120 ml of methylene chloride and 700 ml of carbon tetrachloride is dropwise added 347 ml of a solution of chlorine in carbon tetrachloride (1.6 mole/l) with stirring under cooling at −25° C., and the mixture stirred for 18 minutes, and warmed slowly up to −15° C. After 20 minutes, the mixture is poured into about 2 liter of ice cold aqueous 5% sodium hydrogencarbonate and extracted with methylene chloride. The extract is washed with water, dried on sodium sulfate and concentrated under reduced pressure to yield 66.5 g of the residue, which is purified by chromatography on 280 g of silica gel containing 10% water and eluted with a mixture of benzene and ethyl acetate (9:1-8.5:1.5) to yield 38.38 g of benzyl α-(2α-chloro-3β-methoxalylamino-4-oxoazetidin-1-yl)-α-isopropylideneacetate in 66.6% yield.

NMR: $\delta^{CDCl_3}$ 2.03s3H, 2.30s3H, 3.90s3H, 5.0-5.3dd(8; 1.5 Hz)1H, 5.25s2H, 5.83d(1.5 Hz)1H, 7.40s5H, 7.90d(8 Hz)1H.

EXAMPLE II-2 ($R^1$=—$CH_2$Ph, COB=—COOCH$_3$, Hal=Cl)

To a solution of 16.78 g of methyl 6β-phenylmethoxalylaminopenicillanate in 330 ml of carbon tetrachloride is added a solution of 9.23 g of chlorine in 77 ml of carbon tetrachloride at −20° to −15° C. with stirring, and the mixture stirred for 20 minutes and shaken with an aqueous solution of sodium hydrogencarbonate. The organic layer is separated, washed with water, dried on magnesium sulfate and concentrated under reduced pressure to yield the residue, which is purified by chromatography on 150 g of silica gel containing 10% water and eluted with benzene containing 15% ethyl acetate to yield 14.7 g of methyl α-(2α-chloro-3-phenylmethoxalylamino-4-oxoazetidin-1-yl)-α-isopropylideneacetate in 87% yield.

IR: $\nu_{max}^{CHCl_3}$ 3390, 1790, 1720 cm$^{-1}$.

NMR: $\delta^{CDCl_3}$ 2.10s3H, 2.30s3H, 3.77s3H, 5.17q(8; 1.5 Hz)1H, 5.33s2H, 5.95d(1.5 Hz)1H, 7.42s5H, 8.30d(8 Hz)1H.

EXAMPLE II-3 ($R^1$=$CH_3$, COB=—COOCHPh$_2$, Hal=Cl)

To a solution of 55.88 g of diphenylmethyl 6β-methoxalylaminopenicillanate in 670 ml of carbon tetrachloride is added a solution of 37.58 g of chlorine in 618 ml of carbon tetrachloride under cooling at −15° to −20° C. After 30 minutes, the reaction mixture is shaken with an aqueous solution of sodium hydrogencarbonate, and the organic layer is separated, washed with water, dried on magnesium sulfate and concentrated under reduced pressure to yield the residue, which is chromatographed on 300 g of silica gel containing 10% water and eluted with benzene containing 15 to 20% ethyl acetate to yield 46.82 g of diphenylmethyl α-(2α-chloro-3-methoxalylamino-4-oxoazetidin-1-yl)-α-isopropylideneacetate in 84% yield.

IR: $\nu_{max}^{CHCl_3}$ 3380, 1790, 1720 cm$^{-1}$.

NMR: $\delta^{CDCl_3}$ 2.02s3H, 2.28s3H, 3.83s3H, 5.07q(8; 1.5 Hz)1H, 5.70d(1.5 Hz)1H, 6.85s1H, 7.28s10H, 7.73d(8 Hz)1H.

III. OXAZOLINE FORMATION

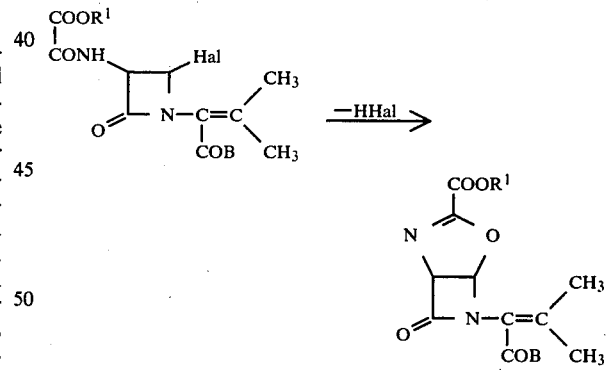

EXAMPLE III-1 ($R^1$=$CH_3$, COB=—COOCH$_2$Ph, Hal=Cl) AgBF$_4$

To a solution of 38.38 g of benzyl α-(2α-chloro-3β-methoxalylamino-4-oxoazetidin-1-yl)-α-isopropylideneacetate in 350 ml of tetrahydrofuran is added 37.84 g of a mass of silvertetrafluoro borate (about 50% purity) at −20° C. with stirring. After 80 minutes, the reaction mixture is poured into 5% aqueous solution of sodium hydrogencarbonate under ice-cooling and extracted with ethyl acetate. The extract is filtered on Hyflo super Cel preliminarily washed with water, and the filtrate washed with water, dried on sodium sulfate and evaporated under reduced pressure to yield 32.78 g of benzyl α-(3-carbomethoxy-7-oxo-4-oxa-2,6-diazabicyclo[3.2.0-]hept-2-en-6-yl)-α-isopropylideneacetate.

IR: $\nu_{max}^{CHCl_3}$ 1790, 1758, 1730, 1631 cm$^{-1}$.

NMR: $\delta^{CDCl_3}$ 1.93s3H, 2.28s3H, 3.93s3H, 5.25ABq(15; 12 Hz)2H, 5.40d(3.5 Hz)1H, 6.17d(3.5 Hz)1H, 7.40s5H.

EXAMPLE III-2 (R$^1$=—CH$_2$Ph, COB=—COOCH$_3$, Hal=Cl) AgBF$_4$

To a solution of 4.80 g of methyl α-(2α-chloro-3β-phenylmethoxalylamino-4-oxoazetidin-1-yl)-α-isopropylideneacetate in 96 ml of tetrahydrofuran is added 4.80 g of silvertetrafluoroborate (50% purity) while stirring and cooling at −20° C., and the mixture stirred for 30 minutes. The reaction mixture is poured into an aqueous solution of sodium hydrogen carbonate and extracted with ethyl acetate. The extract is washed with water, dried on magnesium sulfate and concentrated under reduced pressure. The residue is chromatographed on 80 g of silica gel containing 10% water and eluted with benzene containing 10% ethyl acetate to yield 3.42 g of methyl α-(3-benzyloxycarbonyl-7-oxo-4-oxa-2,6-diazabicyclo[3.2.0]hept-2-en-6-yl)-α-isopropylideneacetate in 78.4% yield.

IR: $\nu_{max}^{CHCl_3}$ 1790, 1760, 1730, 1635 cm$^{-1}$

NMR: $\delta^{CDCl_3}$ 1.87s3H, 2.23s3H, 3.70s3H, 5.39s2H, 5.39d(3 Hz)1H, 6.17d(3 Hz)1H, 7.39s5H.

EXAMPLE III-3 (R$^1$=—CH$_3$, COB=—COOCHPh$_2$, Hal=Cl) ZnCl$_2$

To a solution of 1.41 g of diphenylmethyl α-(2α-chloro-3β-methoxalylamino-4-oxoazetidin-1-yl)-α-isopropylideneacetate in 20 ml of tetrahydrofuran are added 6 ml of ether solution of zinc chloride (0.61 mole/l) and 0.33 ml of N-methylmorpholine, and the mixture stirred at room temperature for 15 minutes, diluted with ethyl acetate, washed with water, dried and then concentrated under reduced pressure to yield 1.371 g of diphenylmethyl α-(3-carbomethoxy-7-oxo-4-oxa-2,6-diazabicyclo[3.2.0]-hept-2-en-6-yl)-α-isopropylideneacetate as crystalline product in 91% yield.

EXAMPLE III-4 (R$^1$=—CH$_3$, COB=—COOCHPh$_2$, Hal=Cl) AgBF$_4$

To a solution of 22.70 g of diphenylmethyl α-(2α-chloro-3β-methoxalylamino-4-oxoazetidin-1-yl)-α-isopropylideneacetate in 230 ml of tetrahydrofuran is added 18.8 g of silvertetrafluoro borate (50% purity) while cooling at −15° to −20° C., and the mixture stirred for 40 minutes. The reaction mixture is poured into an aqueous solution of sodium hydrogencarbonate and extracted with ethyl acetate. The extract is washed with water, dried on magnesium sulfate and concentrated under reduced pressure to yield 20.94 g of diphenylmethyl α-(3-carbomethoxy-7-oxo-4-oxa-2,6-diazabicyclo[3.2.0]hept-2-en-6-yl)-α-isopropylideneacetate in 99% yield.

IR: $\nu_{max}^{CHCl_3}$ 1790, 1755, 1725, 1635 cm$^{-1}$

NMR: $\delta^{CDCl_3}$ 1.88s3H, 2.23s3H, 3.83s3H, 5.30d(3.5 Hz)1H, 6.00d (3.5 Hz)1H, 6.83s1H, 7.27s10H.

EXAMPLE III-5 (R$^1$=CH$_3$, COB=—COOCHPh$_2$, Hal=Cl) other reagents

Diphenylmethyl α-(2α-chloro-3β-methoxalylamino-4-oxoazetidin-1-yl)-α-isopropylideneacetate is dissolved in a solvent and allowed to react with the reagent. The reaction mixture is worked up in a conventional manner to yield the starting compound remaining unchanged and diphenylmethyl α-(3-carbomethoxy-7-oxo-4-oxa-2,6-diazabicyclo[3.2.0]hept-2-en-6-yl)-α-isopropylideneacetate in the ratio as described in the following table.

| Reagent (mole ratio) | Solvent | Reaction temperature | Reaction time (hour) | Starting material: Product |
|---|---|---|---|---|
| SnCl$_2$ (1.2) | glyme | rt | 4.75 | 3:1 |
| SnCl$_2$ (1.4) | THF | rt | 24 | 1:1 |
| SnCl$_2$ (2.8) | THF | rt | 24 | 1:1* |
| SnCl$_2$ (1.2) 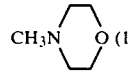 CH$_3$NO (1.0) | THF | rt | 7.5 | 4:1 |
| 10% NaHCO$_3$ | acetone | 0° C. + rt | 2 + 2 | 0:1* |
| ZnCl$_2$ (1.2) | THF | rt | 2 | 1:1 |
| ZnCl$_2$ (1.2) | THF | rt | 24 | 1:1* |
| ZnCl$_2$ (2.4) | THF | rt | 24 | 1:1* |
| ZnCl$_2$ (2.4) | DMF | rt | 5 | 1:0 |
| ZnCl$_2$ (1.2) 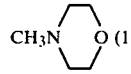 CH$_3$NO (1.0) | THF | rt | 0.25 | 0:1 |

THF : tetrahydrofuran
DMF : N,N-dimethylformamide
rt : room temperature
* : The reaction mixture colors and contains by-product.

IV. REDUCTION YIELDING OXAZOLIDINE

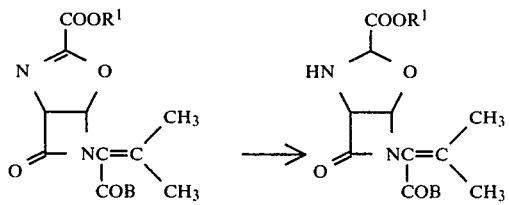

EXAMPLE IV-1 (R$^1$=—CH$_3$, COB=—COOCH$_2$Ph)

A solution of 32.78 g of benzyl α-(3-carbomethoxy-7-oxo-4-oxa-2,6-diaza-bicyclo[3.2.0]hept-2-en-6-yl)-α-isopropylideneacetate in 500 ml of tetrahydrofuran containing 5% water is mixed with aluminium amalgam which has been prepared from 22.95 g of aluminium and 0.5% aqueous solution of mercuric chloride, and the mixture stirred at room temperature for 50 minutes. The reaction mixture is diluted with ethyl acetate and filtrated through a layer of Hyflo Super Cel. The filtrate is dried on sodium sulfate and concentrated under reduced pressure to yield the residue, which is crystallized from ether to yield 22.02 g of benzyl α-(3ξ-carbomethoxy-7-oxo-4-oxa-2,6-diaza-bicyclo[3.2.0]heptan-6-yl)-α-isopropylideneacetate in 61% yield.

mp. 113°–115° C.

IR: $\nu_{max}^{CHCl_3}$ 3366, 1776, 1722, 1633 cm$^{-1}$

NMR: $\delta^{CDCl_3}$ 1.88s3H, 2.15s3H, 3.17brs1H, 3.75s3H, 4.87brs1H, 5.23s2H, 5.65brs1H, 5.80d(4 Hz)1H, 7.40s5H.

[α]$_D$ −94.4°±2.7° C. (c=0.504, CHCl$_3$)

EXAMPLE IV-2 (R$^1$=—CH$_3$, COB=—COOCH$_2$Ph)

A solution of 75 g of benzyl α-(3-carbomethoxy-7-oxo-4-oxa-2,6-diazabicyclo[3.2.0]hept-2-en-6-yl)-α-isopropylideneacetate in 900 ml of tetrahydrofuran containing 5% water is mixed with aluminium amalgam which has been prepared from 26.3 g of aluminium and 2.5% aqueous solution of mercuric chloride, and the mixture stirred under ice-cooling for 20 minutes. The reaction mixture is filtrated through Hyflo Super Cel, diluted with ethyl acetate, washed with an aqueous solution of sodium hydrogencarbonate and water, dried on sodium sulfate, concentrated and then mixed with ether. The resulting crystals are collected by filtration to yield 47.02 g of benzyl α-(3ξ-carbomethoxy-7-oxo-4-oxa-2,6-diazabicyclo[3.2.0]heptan-6-yl)-α-isopropylideneacetate in 62.4% yield.

mp. 113°–115° C.

EXAMPLE IV-3 ($R^1$=—$CH_3$, COB=—COOCH$_2$Ph, Hal=Cl)

In the same manner as described in Examples 1 and 2, 65.5 g of benzyl 6-aminopenicillanate p-toluenesulfonate is methoxalylated to yield 59.9 g of benzyl α-(2α-chloro-3β-methoxalylamino-4-oxazetidin-1-yl)-α-isopropylideneacetate. This is dissolved in 740 ml of tetrahydrofuran and treated with a mixture of 24.24 g of zinc chloride, 16.3 ml of N-methylmorpholine and 226 ml of ether at room temperature in nitrogen atmosphere for 40 minutes. The mixture is then extracted with ethyl acetate to yield 50.79 g of benzyl α-(3-carbomethoxy-7-oxo-4-oxa-2,6-diazabicyclo[3.2.0]hept-2-en-6-yl)-α-isopropylideneacetate. This is treated with aluminium amalgam in tetrahydrofuran and purified by chromatography on silica gel to yield 18.07 g of benzyl α-(3ξ-carbomethoxy-7-oxo-4-oxa-2,6-biazabicyclo[3.2.0]-heptan-6-yl)-α-isopropylideneacetate in 44% yield.

mp. 114°–116° C.

EXAMPLE IV-4 ($R^1$=—$CH_2Ph$, COB=—$COOCH_3$)

To a solution of 5.00 g of methyl α-(3-carbobenzoxy-7-oxo-4-oxa-2,6-diazabicyclo[3.2.0]hept-2-en-6-yl)-α-isopropylideneacetate in 100 ml of tetrahydrofuran containing 5% water is added aluminium amalgam prepared from 4 g of aluminium and 0.5 g of mercuric chloride, and the mixture stirred at room temperature for 1.5 hours. The reaction mixture is dried on magnesium sulfate and concentrated under reduced pressure to yield 4.92 g of methyl α-(3ξ-carbobenzoxy-7-oxo-4-oxa-2,6-diazabicyclo[3.2.0]heptan-6-yl)-α-isopropylideneacetate as crude product in 98.4% yield.

IR: $\nu_{max}^{CHCl_3}$ 3380, 1780, 1730 cm$^{-1}$

NMR: $\delta^{CDCl_3}$ 1.77s3H, 2.07s3H, 3.75s3H, 5.00d(3.5 Hz)1H, 5.17s2H, 5.67s1H, 5.83d(3.5 Hz)1H, 7.40s5H.

EXAMPLE IV-5 ($R^1$=—$CH_3$, COB=—$COOCHPh_2$)

To a solution of 23.0 g of diphenylmethyl α-(3-carbomethoxy-7-oxo-4-oxa-2,6-diazabicyclo[3.2.0]hept-2-en-6-yl)-α-isopropylideneacetate in 480 ml of tetrahydrofuran containing 5% water is added aluminium amalgam prepared from 10 g of aluminium and 250 ml of 0.5% mercuric chloride and the mixture stirred at room temperature for 2 hours, dried on magnesium sulfate and concentrated under reduced pressure. The residue is recrystallized from a mixture of methylene chloride and ether (1:5) to yield 17.5 g of diphenylmethyl α-(3ξ-carbomethoxy-7-oxo-4-oxa-2,6-diazabicyclo[3.2.0]heptan-6-yl)-α-isopropylideneacetate in 76% yield.

mp. 136°–139° C.

IR: $\nu_{max}^{CHCl_3}$ 3370, 1780, 1730, 1710(sh) cm$^{-1}$

NMR: $\delta^{CDCl_3}$ 1.87s3H, 2.13s3H, 3.30-2.70 ml H, 3.70s3H, 4.73d (3.5 Hz)1H, 5.50s1H, 5.67d(3.5 Hz)1H, 6.87s1H, 7.30s10H.

V. N-ACYLATION

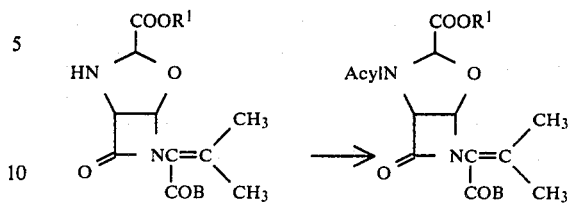

EXAMPLE V-1 ($R^1$=—$CH_3$, COB=—COOCH$_2$Ph, Acyl=PhCH$_2$CO—)

To a solution of 32.6 g of benzyl α-(3ξ-carbomethoxy-7-oxo-4-oxa-2,6-diazabicyclo[3.2.0]heptan-6-yl)-α-isopropylideneacetate in 750 ml of tetrahydrofuran is dropwise added a solution of 9.5 ml of pyridine and 15.1 ml of phenylacetyl chloride in 144 ml of tetrahydrofuran over a period of 15 minutes while maintaining the temperature at −20° C. and stirring under nitrogen atmosphere. The mixture is stirred for 55 minutes, poured into 700 ml of ice water, stirred for 5 minutes and extracted with ethyl acetate. The extract is washed with an aqueous solution of sodium hydrogencarbonate and water, dried on sodium sulfate, and evaporated under reduced pressure to yield 46.4 g of benzyl α-(3ξ-carbomethoxy-2-phenylacetyl-7-oxo-4oxa-2,6-diazabicyclo[3.2.0]heptan-6-yl)-α-isopropylideneacetate as crude product in 107% yield.

IR: $\nu_{max}^{CHCl_3}$ 1787, 1762, 1725, 1674 cm$^{-1}$

NMR: $\delta^{CDCl_3}$ 1.92s3H, 2.20s3H, 3.78s3H, 3.92s2H, 5.15d(4 Hz)1H, 5.23s2H, 6.02d(4 Hz)1H, 6.13s1H, 7.38s5H, 7.42s5H.

EXAMPLE V-2 ($R^1$=—$CH_3$, COB=—COOCH$_2$Ph, Acyl=PhCH$_2$OCO—)

To a solution of 360 mg of benzyl α-(3ξ-carbomethoxy-7-oxo-4-oxa-2,6-diazabicyclo[3.2.0]heptan-6-yl)-α-isopropylideneacetate in 5 ml of tetrahydrofuran are added 0.1 ml of pyridine and then 255 mg of benzyl chloroformate under ice-cooling, and the mixture stirred for 90 minutes, and then mixed with water and ethyl acetate. The organic layer is separated, washed with water, dried and concentrated to yield the residue, which is chromatographed on silica gel containing 10% water to yield 306 mg of benzyl α-(3ξ-carbomethoxy-2-carbobenzoxy-7-oxo-4-oxa-2,6-diazabicyclo[3.2.0]heptan-6-yl)-α-isopropylideneacetate in 61.7% yield.

IR: $\nu_{max}^{CHCl_3}$ 1785, 1750, 1720, 1635 cm$^{-1}$

NMR: $\delta^{CDCl_3}$ 1.88s3H, 2.02s3H, 3.78s3H, 5.97d(5 Hz)1H, 6.07s1H, 5.25 m 4H, 5.37d(5 Hz)1H, 7.4 mlOH.

EXAMPLE V-3 ($R^1$=—$CH_3$, COB=COOCH$_2$Ph, Acyl=PhCO—)

To a solution of 5 g of benzyl α-(3ξ-carbomethoxy-7-oxo-4-oxa-2,6-diazabicyclo[3.2.0]heptan-6-yl)-α-isopropylideneacetate in 100 ml of tetrahydrofuran are dropwise added 1.82 ml of pyridine and a solution of 2.86 g of benzoyl chloride in 20 ml of tetrahydrofuran at 0° C. under nitrogen atmosphere. After 20 minutes, the reaction mixture is warmed up to room temperature. After additional 2 hours, the mixture is diluted with ice water and extracted with ethyl acetate. The extract is washed with an aqueous sodium sulfate and condensed under reduced pressure to yield 7.02 g of benzyl α-(3ξ-carbomethoxy-2-benzoyl-7-oxo-4-oxa-2,6-diazabicyclo[3.2.0]heptan-6-yl)-α-isopropylideneacetate as crude product.

NMR: δCDCl3 1.93s3H, 2.22s3H, 3.82s3H, 5.18s2H, 5.22d(4 Hz)1H, 6.0d(4 Hz)1H, 6.57s1H, 7.2–8.2 ml 1H.

EXAMPLE V-4 (R$^1$=—CH$_3$, COB=—COOCH$_2$Ph, Acyl=PhCH$_2$SO$_2$—)

To a solution of 500 mg of benzyl α-(3ξ-carbomethoxy-7-oxo-4-oxa-2,6-diazabicyclo[3.2.0]heptan-6-yl)-α-isopropylideneacetate in 10 ml of tetrahydrofuran are added 0.27 ml of triethylamine and 343 mg of phenylmethanesulfonyl chloride under ice-cooling in nitrogen atmosphere, and the mixture stirred for 25 minutes. The reaction mixture is poured into ice water and extracted with ethyl acetate, and the extract washed with water, dried on sodium sulfate and concentrated under reduced pressure to yield 756 mg of benzyl α-(3ξ-carbomethoxy-2-phenylmethanesulfonyl-7-oxo-4-oxa-2,6-diazabicyclo[3.2.0]heptan-6-yl)-α-isopropylideneacetate.

NMR: δCDCl3 1.87s3H, 2.17s3H, 3.77s3H, 4.57s2H, 5.23s2H, 5.27d(4 Hz)1H, 5.95d(4 Hz)1H, 6.20s1H, 7.2–7.6 ml OH.

EXAMPLE V-5 (R$^1$=—CH$_2$Ph, COB=—COOCH$_3$, Acyl=PhCH$_2$CO—)

To a solution of 4.90 g of methyl α-(3ξ-carbobenzoxy-7-oxo-4-oxa-2,6-diazabicyclo[3.2.0]heptan-6-yl)-α-isopropylideneacetate in 50 ml of tetrahydrofuran are added 2.4 ml of triethylamine and then 2.5 ml of phenylacetyl chloride under ice-cooling, and the mixture stirred for 30 minutes, poured into water and extracted with ethyl acetate. The extract is washed with water dried on magnesium sulfate and concentrated under reduced pressure. The residue is chromatographed on 150 g of silica gel containing 10% water and eluted with benzene containing 10% ethyl acetate to yield 4.37 g of methyl α-(3ξ-carbobenzoxy-2-phenylacetyl-7-oxo-4-oxa-2,6-diazabicyclo[3.2.0]heptan-6-yl)-α-isopropylideneacetate in 67.2% yield.

IR: ν$_{max}$CHCl3 1795, 1760, 1730, 1675 cm$^{-1}$

NMR: δCDCl3 1.73s3H, 2.08s3H, 3.70s3H, 3.83s2H, 5.13brs3H, 5.93d(3.5 Hz)1H, 6.07s1H, 7.20s5H.

EXAMPLE V-6 (R$^1$=—CH$_3$, COB=—COOCHPh$_2$, Acyl=PhCH$_2$CO—)

To a solution of 16.46 g of diphenylmethyl α-(3ξ-carbomethoxy-7-oxo-4-oxa-2,6-diazabicyclo[3.2.0]heptan-6-yl)-α-isopropylideneacetate in 160 ml of methylene chloride are added 9.6 ml of triethylamine and 9 ml of phenylacetyl chloride under ice-cooling, and the mixture stirred at room temperature for 2 hours. The reaction mixture is then washed with water, dried on magnesium sulfate and concentrated under reduced pressure. The residue is chromatographed on 200 g of silica gel containing 10% water and eluted with benzene containing 10% ethyl acetate to yield 17 to 19 g of diphenylmethyl α-(3ξ-carbomethoxy-2-phenylacetyl-7-oxo-4-oxa-2,6-diazabicyclo[3.2.0]heptan-6-yl)α-isopropylideneacetate in 80 to 90% yield.

IR: ν$_{max}$CHCl3 1790, 1760, 1730, 1675 cm$^{-1}$

NMR: δCDCl3 1.90s3H, 2.17s3H, 3.70s3H, 3.83s2H, 4.97d(3.5 Hz)1H, 5.80d(3.5 Hz)1H, 5.97s1H, 6.80s1H, 7.20s10H.

VI. DEPROTECTION YIELDING FREE CARBOXY

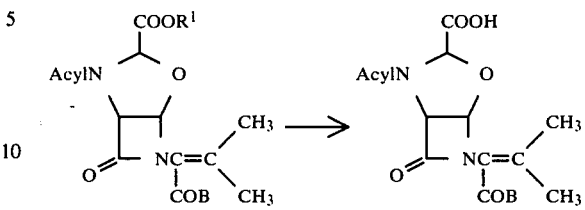

Example VI-1 (R$^1$=—CH$_3$, COB=—COOCH$_2$Ph, Acyl=PhCH$_2$CO—)

To a solution of 39 g of benzyl α-(3ξ-carbomethoxy-2-phenylacetyl-7-oxo-4-oxa-2,6-diazabicyclo[3.2.0]heptan-6-yl)-α-isopropylideneacetate in 628 ml of acetone is added 228 ml of water and then dropwise added 90.8 ml of 1.0 N aqueous solution of sodium hydroxide. The mixture is stirred for 1 hour under ice-cooling, diluted with 630 ml of ice water, covered with ethyl acetate, adjusted to pH 2 with 20% hydrochloric acid and extracted with ethyl acetate. The extract is washed with water, dried on sodium sulfate and concentrated under reduced pressure to yield 41.7 g of benzyl α-(3ξ-carboxy-2-phenylacetyl-7-oxo-4-oxa-2,6-diazabicyclo[3.2.0]heptan-6-yl)-α-isopropylideneacetate as crude product.

IR: ν$_{max}$CHCl3 3500, 1785, 1724, 1704, 1672 cm$^{-1}$

NMR: δCDCl3 1.85s3H, 2.13s3H, 3.87s2H, 5.1–5.2m1H, 5.18s2H, 6.00d(4 Hz)1H, 6.03s1H, 7.30s5H, 7.37s5H, 9.47brs1H.

EXAMPLE VI-2 (R$^1$=CH$_3$, COB=—COOCH$_2$Ph, Acyl=PhCH$_2$OCO—)

To a solution of 1.482 g of benzyl α-(3ξ-carbomethoxy-2-carbobenzoxy-7-oxo-4-oxa-2,6-diazabicyclo[3.2.0]heptan-6-yl)-α-isopropylideneacetate in 20 ml of acetone is added 5 ml of 0.6 M aqueous solution of sodium hydroxide under ice-cooling, and the mixture stirred for 45 minutes, then neutralized with 2N hydrochloric acid and extracted with ethyl acetate. The extract is washed with water, dried and concentrated under reduced pressure to yield 1.27 g of benzyl α-(3ξ-carboxy-2-carbobenzoxy-7-oxo-4-oxa-2,6-diazabicyclo[3.2.0]heptan-6-yl)-α-isopropylideneacetate as crude product in 88.5% yield.

NMR: δCDCl3 1.83s3H, 2.18s3H, 5.88d(5 Hz)1H, 5.97s1H, 6.90s1H, 5.13s2H, 5.17s2H, 7.30m10H.

Example VI-3 (R$^1$=CH$_3$, COB=COOCH$_2$Ph, Acyl=PhCO—)

To a solution of 7.02 g of benzyl α-(3ξ-carbomethoxy-2-benzoyl-7-oxo-4-oxa-2,6-diazabicyclo[3.2.0]heptane-6-yl)-α-isopropylideneacetate dissolved in a mixture of 85 ml of acetone and 26.5 ml of water is added 20 ml of 1.012 N aqueous solution of sodium hydroxide at −3° to −4° C. over a period of an hour and the mixture diluted with water and washed with ethyl acetate. The aqueous layer is separated, adjusted to pH 2.0 with 4 N hydrochloric acid, and then extracted with ethyl acetate. The extract is washed with water, dried on sodium sulfate, and concentrated under reduced pressure to yield 6.34 g of benzyl α-(3ξ-carboxy-2-benzoyl-7-oxo-4-oxa-2,6-diazabicyclo[3.2.0]heptane-6-yl)-α-isopropylideneacetate as foamy material.

IR: $\nu^{CHCl_3}$ 3500, 1788, 1730, 1663 cm$^{-1}$

NMR: $\delta^{CDCl_3}$ 1.93s3H, 2.18s3H, 5.17ABq(14; 13 Hz)2H, 5.20d(4 Hz)1H, 6.03d(4 Hz)1H, 6.57s1H, 7.2–8.2 m11H.

Example VI-4 (R$^1$=CH$_3$, COB=—COOCH$_2$Ph, Acyl=PhCH$_2$SO$_2$—)

To a solution of 756 mg of benzyl α-(3ξ-carbomethoxy-2-phenylmethanesulfonyl-7-oxo-4-oxa-2,6-diazabicyclo[3.2.0]-heptan-6-yl)-α-isopropylideneacetate dissolved in a mixture of 9 ml of acetone and 2.7 ml of water is added 1.85 ml of 1.012 N aqueous solution of sodium hydroxide under ice-cooling. After 15 minutes, the reaction mixture is poured into ice water, mixed with ethyl acetate, adjusted to pH 2 with 2 N-hydrochloric acid under ice-cooling and extracted with ethyl acetate. The extract is washed with water, dried on sodium sulfate, and evaporated under reduced pressure to yield 705 mg of benzyl α-(3ξ-carboxy-2-phenylmethanesulfonyl-7-oxo-4-oxa-2,6-diazabicyclo[3.2.0]heptan-6-yl)-α-isopropylideneacetate.

IR: $\nu_{max}^{CHCl_3}$ 1785, 1728, 1634, 1603 cm$^{-1}$

NMR: $\delta^{CDCl_3}$ 1.83s3H, 2.10s3H, 4.57s2H, 5.22s2H, 5.27d(4 Hz)1H, 5.93d(4 Hz)1H, 6.25s1H, 7.2–7.6m10H, 9.03s1H.

Example VI-5 (R$^1$=PhCH$_2$—, COB=COOCH$_3$, Acyl=PhCH$_2$CO—)

A solution of 4.24 g of methyl α-(3ξ-carbobenzoxy-2-phenylacetyl-7-oxo-4-oxa-2,6-diazabicyclo[3.2.0]heptan-6-yl)-α-isopropylideneacetate dissolved in 64 ml of tetrahydrofuran is catalytically hydrogenated on 1.3 g of 5% palladium carbon under atmospheric pressure. The catalyst is removed by filtration and the filtrate is condensed to yield 3.38 g of methyl α-(3ξ-carboxy-2-phenylacetyl-7-oxo-4-oxa-2,6-diazabicyclo[3.2.0]heptan-6-yl)-α-isopropylideneacetate as crude product in quantitative yield.

IR: $\nu_{max}^{CHCl_3}$ 3500, 1790, 1735, 1685 cm$^{-1}$

NMR: $\delta^{CDCl_3}$ 1.90s3H, 2.20s3H, 3.78s3H, 3.97s2H, 5.30d(3.5 Hz)1H, 6.13d(3.5 Hz)1H, 6.15s1H, 7.40s5H, 8.17brs1H.

Example VI-6 (R$^1$=CH$_3$, COB=—COOCHPh$_2$, Acyl=PhCH$_2$CO—)

To a solution of 11.3 g of diphenylmethyl α-(3ξ-carbomethoxy-2-phenylacetyl-7-oxo-4-oxa-2,6-diazabicyclo[3.2.0]heptan-6-yl)-α-isopropylideneacetate in 230 ml of acetone is added a solution of 900 mg of sodium hydroxide in 36 ml of water under ice-cooling, and the mixture stirred for 1 hour, then diluted with water, acidified with hydrochloric acid, and then extracted with methylene chloride. The extract is washed with water, dried on magnesium sulfate and concentrated under reduced pressure to yield 12.54 g of diphenylmethyl α-(3ξ-carboxy-2-phenylacetyl-7-oxo-4-oxa-2,6-diazabicyclo[3.2.0]heptan-6-yl)-α-isopropylideneacetate as crude product.

NMR: $\delta^{CDCl_3}$ 1.89s3H, 2.17s3H, 3.89s2H, 5.08d(3.5 Hz)1H, 5.92d (3.5 Hz)1H, 6.09s1H, 6.93s1H, 7.33s10H, 7.53brs1H.

This product can be converted into the starting material on treatment with diazomethane in ether.

VII. ACID HALIDE FORMATION
VIII. DIAZOKETONE
IX. HALOMETHEYL KETONE

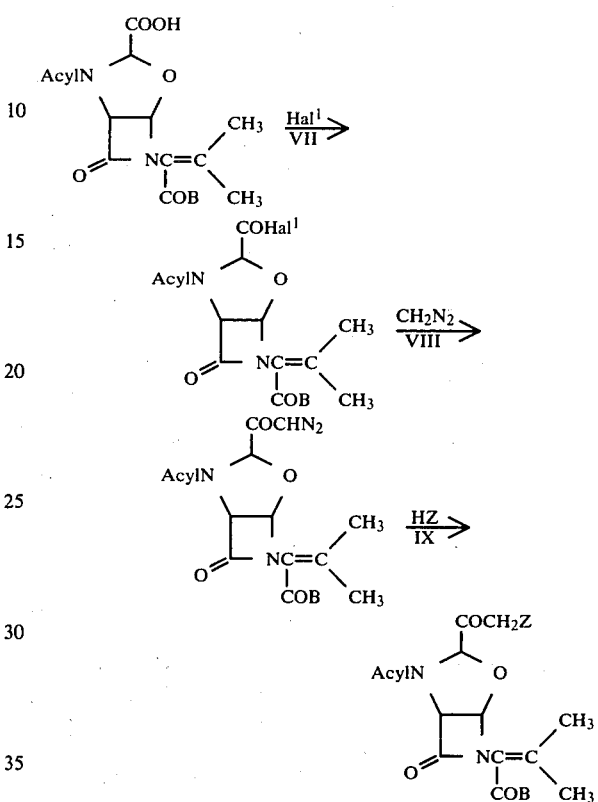

Example IX-1 (COB=—COOCH$_2$Ph, Acyl=PhCH$_2$OCO—, Z=Cl)

To a solution of 435 mg of benzyl α-(3ξ-diazoacetyl-2-carbobenzoxy-7-oxo-4-oxa-2,6-diazabicyclo[3.2.0-]heptan-6-yl)-α-isopropylideneacetate in 4 ml of methylene chloride is added 1 ml of ether containing 16% hydrogen chloride, and the mixture stirred at room temperature for 30 minutes and then concentrated under reduced pressure to yield 433 mg of benzyl α-(3ξ-chloroacetyl-2-carbobenzoxy-7-oxo-4-oxa-2,6-diazabicyclo[3.2.0]heptan-6-yl)-α-isopropylideneacetate as crystals.

IR: $\nu_{max}^{CHCl_3}$ 1785, 1720 cm$^{-1}$

NMR: $\delta^{CDCl_3}$ 1.80s3H, 2.20s3H, 4.43s2H, 5.08m4H, 5.43d(5 Hz)1H, 6.10d(5 Hz)1H, 6.43s1H, 7.3m10H.

Example (VII-VIII)-2 (COB=—COOCH$_2$Ph, Acyl=PhCH$_2$OCO—, Hal$^1$=Cl)

To a solution of 1.44 g of benzyl α-(3ξ-carboxy-2-carbobenzoxy-7-oxo-4-oxa-2,6-diazabicyclo[3.2.0]heptan-6-yl)-α-isopropylideneacetate in 15 ml of benzene is added 0.09 ml of N,N-dimethylformamide and then dropwise added 0.3 ml of oxalyl chloride under ice-cooling, and the mixture stirred at room temperature for 30 minutes. The resulting solution of benzyl α-(3ξ-chlorocarbonyl-2-carbobenzoxy-7-oxo-4-oxa-2,6-diazabicyclo[3.2.0]heptan-6-yl)-α-isopropylideneacetate is concentrated under reduced pressure to yield the residue, which is dissolved in 10 ml of methylene chloride and mixed with ether solution of diazomethane under ice-cooling, and then stirred at room temperature for 30 minutes. The mixture is concentrated under reduced pressure to yield 1.519 g of the residue, which is purified by chromatography on silica gel containing 10% water to yield 886 mg of benzyl α-(3ξ-diazoacetyl-2-carbobenzoxy-7-oxo-4-oxa-2,6-diazabicyclo[3.2.0-]heptan-6-yl)-α-isopropylideneacetate as yellow solid in 58.6% yield.

IR: $\nu_{max}^{CHCl_3}$ 2200, 1780, 1720, 1650 cm$^{-1}$

NMR: $\delta^{CDCl_3}$ 1.87s3H, 2.18s3H, 5.05m4H, 5.43d(5 Hz)1H, 5.75s1H, 6.05d(5 Hz)1H, 6.08s1H, 7.3m10H.

Example (VII, VIII, IX)-3 (COB=—COOCH$_3$, Acyl=PhCH$_2$CO—, Hal$^1$=Cl, Z=Cl)

To a solution of 1.45 g of methyl α-(3ξ-carboxy-2-phenylacetyl-7-oxo-4-oxa-2,6-diazabicyclo[3.2.0]heptan-6-yl)-α-isopropylideneacetate in 7 ml of methylene chloride is added 1.2 ml of thionyl chloride, and the mixture refluxed under heating for 2 hours and concentrated under reduced pressure. The resulting residue [methyl α-(3ξ-chlorocarbonyl-2-phenylacetyl-7-oxo-4-oxa-2,6-diazabicyclo[3.2.0]heptan-6-yl)-α-isopropylideneacetate] is dissolved in 20 ml of tetrahydrofuran and mixed with 15 ml of ether solution of diazomethane which has been prepared from 1.5 g of nitrosomethylurea, and the mixture is kept at room temperature for 30 minutes. Into the resulting solution of methyl α-(3ξ-diazoacetyl-2-phenylacetyl-7-oxo-4-oxa-2,6-diazabicyclo[3.2.0]heptn-6-yl)-α-isopropylideneacetate is introduced hydrogen chloride gas under ice-cooling until the spot of diazo ketone disappears. The mixture is concentrated under reduced pressure, and the residue is purified by chromatography on 17 g of silica gel containing 10% water and eluted with benzene containing 10% ethyl acetate to yield 1.19 g of methyl α-(3ξ-chloroacetyl-2-phenylacetyl-7-oxo-4-oxa-2,6-diazabicyclo[3.2.0]heptan-6-yl)-α-isopropylideneacetate in 75.3% yield.

IR: $\nu_{max}^{CHCl_3}$ 1790, 1725, 1705, 1670 cm$^{-1}$

NMR: $\delta^{CDCl_3}$ 1.83s3H, 2.15s3H, 3.77s3H, 3.92s2H, 4.37s2H, 5.25d(3.5 Hz)1H, 6.10d(3.5 Hz)1H, 6.29s1H, 7.37s5H.

Example (VII, VIII, IX)-4 (COB=—COOCHPh$_2$, Acyl=PhCH$_2$CO—, Hal$^1$=Cl, Z=Cl)

To a solution of 1.774 g of diphenylmethyl α-(3ξ-carboxy-2-phenylacetyl-7-oxo-4-oxa-2,6-diazabicyclo[3.2.0]heptan-6-yl)-α-isopropylideneacetate dissolved in a mixture of 18 ml of benzene and 0.1 ml of N,N-dimethylformamide is added 0.43 ml of oxalyl chloride, and the mixture stirred at room temperature for 30 minutes and then concentrated under reduced pressure. The residue (diphenylmethyl α-(3ξ-chlorocarbonyl-2-phenylacetyl-7-oxo-4-oxa-2,6-diazabicyclo[3.2.0]heptan-6-yl)-α-isopropylideneacetate) is dissolved in 10 ml of methylene chloride and mixed with 15 ml of ether solution of diazomethane, which has been prepared from 1.5 g of nitrosomethylurea, under ice-cooling, and the mixture stirred for 30 minutes. To the resulting solution of diphenylmethyl α-(3ξ-diazoacetyl-2-phenylacetyl-7-oxo-4-oxa-2,6-diazabicyclo[3.2.0]heptan-6-yl)-α-isopropylideneacetate is is added an ether solution of hydrogen chloride until the spot of diazoketone disappears, and the mixture concen rated under reduced pressure. The residue is purified by chromatography on 40 g of silica gel containing 10% water and eluted with benzene containing 10% ethyl acetate to yield 1.59 g of diphenylmethyl α-(3ξ-chloroacetyl-2-phenylacetyl-7-oxo-4-oxa-2,6-diazabicyclo[3.2.0]heptan-6-yl)-α-isopropylideneacetate in 84.7% yield.

IR: $\nu_{max}^{CHCl_3}$ 1785, 1730, 1670 cm$^{-1}$

NMR: $\delta^{CDCl_3}$ 1.80s3H, 2.12s3H, 3.78s2H, 4.25s2H, 5.00d(3.5 Hz)1H, 5.83d(3.5 Hz)1H, 6.13s1H, 6.85s1H, 7.23s10H.

Example IX-5 (COB=—COOCHPh$_2$, Acyl=PhCH$_2$CO—, Z=OAc)

To a solution of 200 mg of diphenylmethyl α-(3ξ-diazoacetyl-2-phenylacetyl-7-oxo-4-oxa-2,6-diazabicyclo[3.2.0]-heptan-6-yl)-α-isopropylideneacetate in 2 ml of acetic acid is added 0.045 ml of boron trifluoride etherate. After the termination of gas evolution, the reaction mixture is poured into ice water and extracted with ethyl acetate. The extract is washed with water, an aqueous solution of sodium hydrogencarbonate and then water, dried on sodium sulfate and evaporated. The residue (205 mg) is purified by thin-layer chromatography to yield 65 mg of diphenylmethyl α-(3ξ-acetoxyacetyl-2-phenylacetyl-7-oxo-4-oxa-2,6-diazabicyclo[3.2.0]heptan-6-yl)-α-isopropylideneacetate in 30% yield.

IR: $\nu_{max}^{CHCl_3}$ 1788, 1752, 1730sh, 1675 cm$^{-1}$

NMR: $\delta^{CDCl_3}$ 1.80s3H, 2.03s3H, 2.15s3H, 3.80s2H, 4.80s2H, 5.00br1H, 5.82d(4 Hz)1H, 6.08s1H, 6.80s1H, 7.20s10H.

X. REDUCTION YIELDING METHYLKETONE

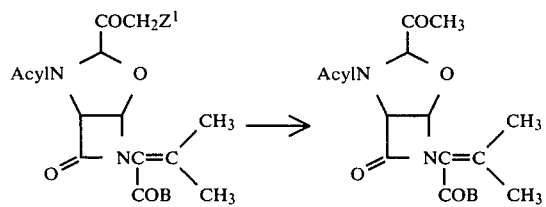

Example (VII, VIII, IX, X)-1 (COB=COOCH$_2$Ph, Acyl=PhCH$_2$CO—, Hal$^1$=Cl, Z=Cl→H)

To a solution of 10 g of benzyl α-(3ξ-carboxy-2-phenylacetyl-7-oxo-4-oxa-2,6-diazabicyclo[3.2.0]heptan-6-yl)-α-isopropylideneacetate in 120 ml of benzene are added 0.25 ml of N,N-dimethylformamide and 2.2 ml of oxalyl chloride, and the mixture stirred at room temperature for 45 minutes. The resulting solution of benzyl α-(3ξ-chlorocarbonyl-2-phenylacetyl-7-oxo-4-oxa-2,6-diazabicyclo[3.2.0]heptan-6-yl)-α-isopropylideneacetate is concentrated to about ½ volume, then dropwise added to a solution of diazomethane in 250 ml of ether (which has been prepared from 13 g of nitrosomethyl-urea) under ice-cooling, and stirred for 20 minutes. The resulting solution of benzyl α-(3ξ-diazoacetyl-2-phenylacetyl-7-oxo-4-oxa-2,6-diazabicyclo[3.2.0]heptan-6-yl)-α-isopropylideneacetate is mixed with 10 ml of ether containing 16% hydrogen chloride, and after 85 minutes, the mixture is concentrated under reduced pressure. The residue [benzyl α-(3ξ-chloroacetyl-2-phenylacetyl-7-oxo-4-oxa-2,6-diazabicyclo[3.2.0]heptan-6-yl)-α-isopropylideneacetate (IR: $\nu_{max}^{CHCL_3}$ 1786, 1724, 1674 cm$^{-1}$)], is dissolved in 100 ml of acetic acid and mixed with 10 g of zinc powder which has preliminarily been washed with hydrochloric acid, water, ethanol and ether, and stirred at room temperature for 1.5 hours. The reaction mixture is filtrated, and the filtrate poured into 90 ml of ice water and extracted with methylene chloride. The extract is washed with water, an aqueous solution of sodium hydrogencarbonate and then water, dried on sodium sulfate and concentrated under reduced pressure. The residue (9.68 g) is purified by chromatography on 200 g of silica gel containing 10% water and eluted with a mixture of benzene and ethyl acetate (7:1) to yield 7.208 g of benzyl α-(3ξ-acetyl-2-phenylacetyl-7-oxo-4-oxa-2,6-diazabicyclo[3.2.0]-heptan-6-yl)-α-isopropylideneacetate in 79.7% yield.

IR: $\nu_{max}^{CHCl_3}$ 1785, 1727, 1703, 1670, 1603, 1585 cm$^{-1}$

NMR: $\delta^{CDCl_3}$ 1.85s3H, 2.18s3H, 2.28s3H, 3.92s2H, 5.15d(4 Hz)1H, 5.23ABq(14; 13 Hz)2H, 6.03d(4 Hz)1H, 6.15s1H, 7.38s5H, 7.42s5H.

Example X-2 (COB=—COOCH$_2$Ph, Acyl=PhCH$_2$OCO—, Z=Cl→H)

To a solution of 433 mg of benzyl α-(3ξ-chloroacetyl-2-carbobenzoxy-7-oxo-4-oxa-2,6-diazabicyclo[3.2.0]-heptan-6-yl)-α-isopropylideneacetate dissolved in a mixture of 4 ml of methylene chloride and 4 ml of acetic acid is added 450 mg of zinc powder, and the mixture stirred at room temperature for 1 hour. The reaction mixture is filtrated and the filtrate diluted with water and extracted with methylene chloride. The extract is washed with water, dried and evaporated to yield 375 mg of benzyl α-(3ξ-acetyl-2-carbobenzoxy-7-oxo-4-oxa-2,6-diazabicyclo[3.2.0]heptan-6-yl)-α-isopropylideneacetate as an oily material in 98% yield.

NMR: $\delta^{CDCl_3}$ 1.80s3H, 2.17s3H, 2.26S3H, 5.17m4H, 5.37d(5 Hz)1H, 5.97s1H, 6.0d(5 Hz)1H, 7.3m10H.

Example (VII, VIII, IX, X)-3 (COB=—COOCH$_2$Ph, Acyl=PhCO—, Z=Cl→H)

To a solution of 5.8 g of benzyl α-(3ξ-carboxy-2-benzoyl-7-oxo-4-oxa-2,6-diazabicyclo[3.2.0]heptan-6-yl)-α-isopropylideneacetate dissolved in a mixture of 70 ml of benzene and 0.14 ml of N,N-dimethylformamide is added 1.33 ml of oxalyl chloride at room temperature under nitrogen atmosphere, and the mixture allowed to stand for 30 minutes, and concentrated to ½ volume. The resulting solution of benzyl α-(3ξ-chlorocarbonyl-2-benzoyl-7-oxo-4-oxa-2,6-diazabicyclo[3.2.0]heptan-6-yl)-α-isopropylidene-acetate is mixed under ice-cooling with an ether solution of diazomethane prepared from 4 g of N-nitrosomethylurea. The resulting solution of benzyl α-(3ξ-diazoacetyl-2-benzoyl-7-oxo-4-oxa-2,6-diazabicyclo[3.2.0]heptan-6-yl)-α-isopropylideneacetate is mixed with 2.1 ml of ether containing 0.47 g of hydrogen chloride at 0° C., and after 2 hours, evaporated to yield 6.3 g of benzyl α-(3ξ-chloroacetyl-2-benzoyl-7-oxo-4-oxa-[3.2.0]heptan-6-yl)-α-isopropylideneacetate as an yellow-brown oil.

This product dissolved in 60 ml of acetic acid is mixed with 5.8 g of activated zinc under nitrogen gas at room temperature, and the mixture stirred for 25 minutes, poured into ice water and extracted with ethyl acetate. The extract is washed with an aqueous solution of sodium hydrogencarbonate and water, dried on sodium sulfate and evaporated to yield 5.04 g of benzyl α-(3ξ-acetyl-2-benzoyl-7-oxo-4-oxa-2,6-diazabicyclo[3.2.0-]heptan-6-yl)-α-isopropylideneacetate. This is purified by chromatography on 200 g of silica gel containing 10% water and eluted with a mixture of benzene and ethyl acetate (5:1) to yield 2.9 g of the pure product in 46.5% yield.

IR: $\nu_{max}^{CHCl_3}$ 1785, 1732, 1660 cm$^{-1}$

NMR: $\delta^{CDCl_3}$ 1.85s3H, 2.17s3H, 2.30s3H, 5.17d(4 Hz)1H, 5.22ABq (15;12 Hz)2H, 6.05d(4 Hz)1H, 6.50s1H, 7.2-8.1m11H.

$[\alpha]_D^{21.5}$ −91.7° (c=0.412, CHCl$_3$)

Example (VII, VIII, IX, X)-4 (COB=—COOCH$_2$Ph, Acyl=PhCH$_2$SO$_2$—, Hal$^1$=Cl, Z=Cl→H)

To a solution of 600 mg of benzyl α-(3ξ-carboxy-2-phenylmethanesulfonyl-7-oxo-4-oxa-2,6-diazabicyclo[3.2.0]heptan-6-yl)-α-isopropylideneacetate in 12 ml of benzene are added 40 μl of dimethylformamide and 0.12 ml of oxalyl chloride, and the mixture kept at room temperature for 20 minutes. The reaction mixture is concentrated to ⅓ volume, diluted with 6 ml of methylene chloride, and mixed with an ether solution of diazomethane under cooling at −20° C. After 30 minutes, the reaction mixture is mixed with 1 ml of ether solution containing 0.24 g of hydrogen chloride at −20° C., and after 50 minutes, evaporated in vacuo under ice-cooling. The residue, benzyl α-(3ξ-chloroacetyl-2-phenylmethanesulfonyl-7-oxo-4-oxa-2,6-diazabicyclo[3.2.0-]heptan-6-yl)-α-isopropylideneacetate, is dissolved in 6 ml of glacial acetic acid, mixed with 600 mg of activated zinc powder, and stirred at room temperature for 140 minutes. The reaction mixture, from which zinc powder is removed, is poured into ice water and extracted with methylene chloride. The extract is washed with water, an aqueous solution of sodium hydrogencarbonate and then water, dried on sodium sulfate and concentrated under reduced pressure to yield 563 mg of the residue, which is purified by chromatography on 17 g of silica gel containing 10% water and eluted with a mixture of benzene and ethyl acetate (7:1) to yield 377 mg of benzyl α-(3ξ-acetyl-2-phenylmethanesulfonyl-7-oxo-4-oxa-2,6-diazabicyclo[3.2.0]heptan-6-yl)-α-isopropylideneacetate in 64% over-all yield from Example 48.

IR: $\nu_{max}^{CHCl_3}$ 1790, 1735, 1634, 1608 cm$^{-1}$

NMR: $\delta^{CHCl_3}$ 1.77s3H, 2.13s3H, 2.18s3H, 4.57s3H, 5.17d(4 Hz)1H, 5.23ABq(14;12 Hz)2H, 5.97d(4 Hz)1H, 7.2-7.6m10H.

Example X-5 (COB=—COOCH$_3$, Acyl=PhCH$_2$CO—, Z=Cl→H)

To a solution of 1.28 g of methyl α-(3ξ-chloroacetyl-2-phenylacetyl-7-oxo-4-oxa-2,6-diazabicyclo[3.2.0]heptan-6-yl)-α-isopropylideneacetate in 13 ml of acetic acid is added 2 g of zinc powder, and the mixture stirred at room temperature for 1 hour. The reaction mixture is filtrated, and the filtrate poured into water and extracted with methylene chloride. The extract is washed with water, dried on magnesium sulfate and concentrated under reduced pressure to yield 1.125 g of α-(3ξ-acetyl-2-phenylacetyl-7-oxo-4-oxa-2,6-diazabicyclo[3.2.0]heptan-6-yl)-α-isopropylideneacetate in approximately 95.7% yield.

IR: $\nu_{max}^{CHCl_3}$ 1780, 1730, 1670 cm$^{-1}$

NMR: $\delta^{CDCl_3}$ 1.82s3H, 2.17s3H, 2.27s3H, 3.78s3H, 3.92s2H, 5.30d(3.5 Hz)1H, 6.10d(3.5 Hz)1H, 6.13s1H, 7.37s5H.

Example X-6 (COB=—COOCHPh$_2$, Acyl=PhCH$_2$CO—, Z=Cl→H)

To a solution of 1.59 g of diphenylmethyl α-(3ξ-chloroacetyl-2-phenylacetyl-7-oxo-4-oxa-2,6-diazabicyclo[3.2.0]heptan-6-yl)-α-isopropylideneacetate in 16 ml of acetic acid is added 1.5 g of zinc powder, and the mixture stirred at room temperature for 1 hour, then poured into water and extracted with methylene chloride. The extract is washed with water, dried on magnesium sulfate and concentrated under reduced pressure. The residue is purified by chromatography on 30 g of silica gel containing 10% water and eluted with benzene containing 10% ethyl acetate to yield 1.21 g of diphenylmethyl α-(3ξ-acetyl-2-phenylacetyl-7-oxo-4-oxa-2,6-diazabicyclo[3.2.0]heptan-6-yl)-α-isopropylideneacetate in 81% yield.

IR: $\nu_{max}^{CDCl_3}$ 1785, 1730, 1670 cm$^{-1}$

NMR: $\delta^{CDCl_3}$ 1.82s3H, 2.15s3H, 2.22s3H, 3.87s2H, 5.07d(3.5 Hz)1H, 5.90d(3.5 Hz)1H, 6.10s1H, 6.97s1H, 7.33s10H.

XI. OXAZOLIDINE CLEAVAGE

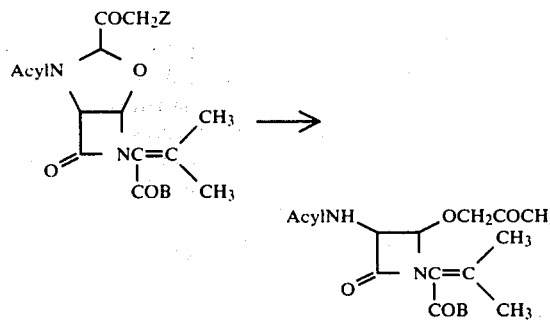

Example XI-1 (COB=—COOCH$_2$Ph, Acyl=PhCH$_2$CO—, Z=H)

To a solution of 550 mg of benzyl α-(3ξ-acetyl-2-phenylacetyl-7-oxo-4-oxa-2,6-diazabicyclo[3.2.0]heptan-6-yl)-α-isopropylideneacetate in 8 ml of tetrahydrofuran is added 5% palladium carbon, and the mixture catalytically hydrogenated under atmospheric pressure for 2 hours. The insoluble material is removed by filtration, and the filtrate concentrated under reduced pressure. The residue (471 mg) is crystallized from a mixture of ether and petroleum ether to yield 421 mg of α-(3ξ-acetyl-2-phenylacetyl-7-oxo-4-oxa-2,6-diazabicyclo[3.2.0]-heptan-6-yl)-α-isopropylideneacetic acid in 95% yield.

mp. 80°-88° C.

IR: $\nu_{max}^{CHCl_3}$ 1783, 1741, 1674, 1626, 1498, 1455 cm$^{-1}$

NMR: $\delta^{CDCl_3}$ 1.87s3H, 2.22s3H, 2.27s3H, 3.92s2H, 5.23d(4 Hz)1H, 5.80d(4 Hz)1H, 7.33s5H, 7.52s1H.

Example XI-2 (COB=—COOCH$_2$Ph, Acyl=PhCH$_2$CO—, Z=H)

A solution of 1 g of benzyl α-(3ξ-acetyl-2-phenylacetyl-7-oxo-4-oxa-2,6-diazabicyclo[3.2.0]heptan-6-yl)-α-isopropylideneacetate dissolved in a mixture of 8 ml of t-butanol and 2 ml of trifluoroacetic acid is mixed under ice-cooling with aluminium amalgam prepared from 3 g of aluminium, and the mixture stirred for 2 hours. The supernatant solution from which amalgam has been removed, is mixed with water and extracted with methylene chloride. The extract is washed with an aqueous solution of sodium hydrogencarbonate, water, and a saturated aqueous solution of sodium chloride, dried on magnesium sulfate and evaporated. The residue (737 mg) is chromatographed on silica gel containing 10% water to yield 228 mg of the starting material and 326 mg of benzyl α-(2β-acetonyloxy-3β-phenylacetamido-4-oxoazetidin-1-yl)-α-isopropylideneacetate in 32.2% yield.

Example XI-3 (COB=—COOCH$_2$Ph, Acyl=PhCH$_2$CO—, Z=H)

A solution of 9.62 g of benzyl α-(3ξ-acetyl-2-phenylacetyl-7-oxo-4-oxa-2,6-diazabicyclo[3.2.0]heptan-6-yl)-α-isopropylideneacetate in 20 ml of benzene is diluted with 254 ml of t-butanol and then mixed with 48.4 g of active zinc powder. Then 22 ml of 16% hydrogen chloride in ether is dropwise added thereto with stirring in nitrogen atmosphere. After the termination of dropwise addition, the mixture is filtrated, and the filtrate shaken with water and ethyl acetate. The organic layer is separated, washed with water, dried on sodium sulfate and concentrated under reduced pressure. The residue (11.2 g) is chromatographed on 500 g of silica gel containing 10% water to yield 1.03 g of the starting material and 4.3 g of benzyl α-(2β-acetonyloxy-3β-phenylacetamido-4-oxoazetidin-1-yl)-α-isopropylideneacetate in 44.7% yield.

IR: $\nu_{max}^{CHCl_3}$ 3420, 1778, 1724, 1684 cm$^{-1}$

NMR: $\delta^{CDCl_3}$ 1.90s3H, 1.97s3H, 2.25s3H, 3.61s2H, 3.85brs2H, 5.05–5.40m4H, 6.35d(8 Hz)1H, 7.33s5H, 7.28s5H.

$[\alpha]_D^{22.5} < 8.0 \pm 1.0°$ (c=0.476, CHCl$_3$)

Example XI-4 (COB=—COOCH$_2$Ph, Acyl=PhCH$_2$CO—, Z→H)

A solution of 100 mg of benzyl α-(3ξ-acetyl-2-phenylacetyl-7-oxo-4-oxa-2,6-diazabicyclo[3.2.0]heptan-6-yl)-α-isopropylideneacetate in 1 ml of trifluoroacetic acid is mixed with aluminum amalgam prepared from 300 mg of aluminium, and the mixture stirred at room temperature for 2 hours, then poured into ice water and extracted with methylene chloride. The extract is washed with water, dried on sodium sulfate and concentrated to yield 68 mg of the residue containing 60 to 70% benzyl α-(2β-acetonyloxy-3β-phenylacetamido-4-oxoazetidin-1-yl)-α-isopropylideneacetate.

The same reaction as mentioned above is carried out in a mixture of ethanol or t-butanol and formic acid (9:1) in place of trifluoroacetic acid to yield about 60 to 90 mg of the residue containing about 30% of the objective compound.

Example XI-5 (COB=-COOCH$_2$Ph, Acyl=PhCO-, Z=H)

To a solution of 107 mg of benzyl α-(3ξ-acetyl-2-benzoyl-7-oxo-4-oxa-2,6-diazabicyclo[3.2.0]heptan-6-yl)-α-isopropylideneacetate dissolved in a mixture of 0.5 ml of benzene and 3 ml of t-butanol is added 550 mg of activated zinc powder at 15° C. under nitrogen atmosphere, and then dropwise added 0.75 ml of ether containing 16% hydrogen chloride. The reaction mixture is poured into ice water and extracted with methylene chloride. The extract is washed with water, dried on sodium sulfate and evaporated. The residue (107 mg) is purified by chromatography on silica gel containing 10% water to yield 45 mg of benzyl α-(2β-acetonyloxy-3β-benzamido-4-oxoazetidin-1-yl)-α-isopropylideneacetate as colorless syrup in 42% yield.

IR: $\nu_{max}^{CHCl_3}$ 3430, 1775, 1720, 1664, 1600, 1580 cm$^{-1}$

NMR: $\delta^{CDCl_3}$ 1.93s3H, 2.00s3H. 2.23s3H, 4.03s2H, 5.17ABq (14;12 Hz)2H, 5.20d(4 Hz)1H, 5.23dd(8;4 Hz)1H, 7.17d (8 Hz)1H, 7.2–8.0 m11H.

$[\alpha]_D^{23} - 12.4 \pm 1.1°$ (c=0.491, CHCl$_3$)

Example XI-6 (COB=—COOCH$_2$Ph, Acyl=PhCO-, Z=H)

A solution of 100 mg of benzyl α-(3ξ-acetyl-2-benzoyl-7-oxo-4-oxa-2,6-diazabicyclo[3.2.0]heptan-6-yl)-α-isopropylideneacetate dissolved in 1 ml of a mixture of trifluoroacetic acid and t-butanol (1:4) is mixed with aluminium amalgam prepared from 300 mg of aluminium, and the mixture stirred at room temperature for 3.5 hours. The reaction mixture is diluted with methylene chloride, washed with water, dried on sodiumsulfate and evaporated to yield 69 mg of a residue, which is a mixture of the starting material and benzyl α-(2β-acetonyloxy-3β-benzamido-4-oxoazetidin-1-yl)-α-isopropylideneacetate (about 2:3).

Example XI-7 (COB=—COOCH$_2$Ph, Acyl=PhCH$_2$SO$_2$-, Z=H)

To a solution of 67 mg of benzyl α-(3ξ-acetyl-2-phenylmethanesulfonyl-7-oxo-4-oxa-2,6-diazabicyclo[3.2.0]heptan-6-yl)-α-isopropylideneacetate dissolved in a mixture of 0.3 ml of benzene and 2 ml of t-butanol is added 335 mg of activated zinc powder under nitrogen atmosphere while the reaction temperature is maintained at 10° C. Then 0.3 ml of ether containing 16% hydrogen chloride is dropwise added thereto and the mixture stirred at room temperature for 40 minutes. The reaction mixture, from which zinc powder is removed, is poured into water and extracted with ethyl acetate. The extract is washed with water, dried on sodium sulfate and concentrated under reduced pressure to yield 65 mg of benzyl α-(2β-acetonyloxy-3β-phenylmethylsulfonylamino-4-oxoazetidin-1-yl)-α-isopropylideneacetate. This is purified by thin layer chromatography to yield 30.3 mg of the pure product in 45.2% yield.

IR: $\nu_{max}^{CHCl_3}$ 3370, 1782, 1730, 1634 cm$^{-1}$

NMR: $\delta^{CDCl_3}$ 2.02s6H, 2.28s3H, 4.13s2H, 4.43s2H, 4.67q(10;4 Hz)1H, 5.20d(4 Hz)1H, 5.25ABq(15;12 Hz)2H, 5.45d(10 Hz)1H, 7.3–7.6 ml0H.

Example XI-8 (COB=—COOCH$_3$, Acyl=PhCH$_2$CO-, Z=H)

To a solution of 300 mg of methyl α-(3ξ-acetyl-2-phenylacetyl-7-oxo-4-oxa-2,6-diazabicyclo[3.2.0]heptan-6-yl)-α-isopropylideneacetate in 3 ml of acetic acid is added 1.5 g of activated zinc powder and then dropwise added 3 ml of acetic acid saturated with hydrogen chloride at room temperature, and the mixture stirred for 30 minutes, then poured into water and extracted with methylene chloride. The extract is washed with water, dried on magnesium sulfate and evaporated. The residue is purified by chromatography on silica gel containing 10% water and eluted with benzene containing 20 to 40% ethyl acetate to yield the starting material remaining unchanged and methyl α-(2β-acetonyloxy-3β-phenylacetamido-4-oxoazetidin-1-yl)-α-isopropylideneacetate in 20 to 30% yield.

IR: $\nu_{max}^{CHCl_3}$ 3400, 1780, 1730, 1680 cm$^{-1}$

NMR: $\delta^{CDCl_3}$ 1.97s6H, 2.23s3H, 3.63s2H, 3.73s3H, 3.97s2H, 5.26d(3.5 Hz)1H, 5.33q(8;3.5 Hz)1H, 6.74d(8 Hz)1H, 7.33s5H.

Example (X, XI)-9 (COB=—COOCH$_3$, Acyl=PhCH$_2$CO-, Z=H)

To a solution of 233 mg of methyl α-(3ξ-chloroacetyl-2-phenylacetyl-7-oxo-4-oxa-2,6-diazabicyclo[3.2.0]heptan-6-yl)-α-isopropylideneacetate in 2 ml of acetic acid is added 1 g of activated zinc powder and then dropwise added 2 ml of acetic acid saturated with hydrogen chloride at room temperature. The mixture is stirred for 30 minutes, poured into water and extracted with methylene chloride. The extract is washed with water, dried on magnesium sulfate and concentrated under reduced pressure to yield the residue containing about 40% methyl α-(2β-acetonyloxy-3β-phenylacetamido-4-oxoazetidin-1-yl)-α-isopropylideneacetate.

Example XI-10 (COB=—COOCH$_3$, Acyl=PhCH$_2$CO-, Z=H)

A solution of 208 mg of methyl α-(3ξ-acetyl-2-phenylacetyl-7-oxo-4-oxa-2,6-diazabicyclo[3.2.0]heptan-6-yl)-α-isopropylideneacetate in 2 ml of acetic acid is mixed with aluminum amalgam prepared from 0.2 g of aluminium, and the mixture stirred at room temperature for 1 hour, poured into water and extracted with methylene chloride. The extract is washed with water, dried and concentrated under reduced pressure to yield 166 mg of the residue containing about 50% methyl α-(2β-acetonyloxy-3β-phenylacetamido-4-oxoazetidin-1-yl)-α-isopropylideneacetate.

Example XI-11 (COB=—COOCHPh$_2$, Acyl=PhCH$_2$CO-, Z=H)

To a solution of 544 mg of diphenylmethyl α-(3ξ-acetyl-2-phenylacetyl-7-oxo-4-oxa-2,6-diazabicyclo[3.2.0]heptan-6-yl)-α-isopropylideneacetate in 5.5 ml of acetic acid is added aluminium amalgam prepared from 0.5 g of aluminium and 5 ml of 0.5% aqueous solution of mercuric chloride, and the mixture stirred at room temperature for 2 hours. After the reaction completed, the mixture is poured into water and extracted with methylene chloride. The extract is washed with water, dried and filtrated. The filtrate is concentrated to yield the residue, which is purified by chromatography on silica gel to yield 120 mg of the starting material and 191 mg of diphenylmethyl α-(2β-acetonyloxy-3β-phenylacetamido-4-oxoazetidin-1-yl)-α-isopropylideneacetate.

IR: $\nu_{max}^{CHCl_3}$ 3425, 1774, 1735sh, 1720, 1676, 1510 cm$^{-1}$

NMR: $\delta^{CDCl_3}$ 1.83s3H, 1.97s3H, 2.23s3H, 3.60s2H, 3.60+3.97q (8 Hz)2H, 5.03d(4 Hz)1H, 5.27dd(8;4 Hz)1H, 6.50d(8 Hz) 1H, 6.93s1H, 7.30+7.33 ml5H.

What we claim is:

1. A compound of the following formula:

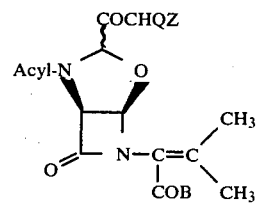

wherein Acyl is a member selected from the group consisting acetyl, cyclopentylcarbonyl, cyclopentylacetyl, cyclohexylcarbonyl, cyclohexylacetyl, cyclohexylpropionyl, cyclohexadienylacetyl, cycloheptylcarbonyl, cycloheptylacetyl, cycloheptylpropionyl, chloroacetyl, chloropropionyl, fluoroacetyl, bromoacetyl, difluoroacetyl, dichloroacetyl, chloropropionyl, hexenoyl, methoxyacetyl, isopropoxyacetyl, pentyloxyacetyl, hexyloxyacetyl, cyclohexyloxyacetyl, phenoxyacetyl, phenoxypropionyl, phenoxybutyryl, diphenoxyacetyl, methylthiophenoxyacetyl, tetrahydronaphthyloxyacetyl, methylthioacetyl, butylthioacetyl, cyclohexylthioacetyl, phenylthioacetyl, phenylthiopropionyl, fluorophenylthioacetyl, chlorophenylthioacetyl, pyridylthioacetyl, pyrimidylthioacetyl, benzoyl, methylbenzoyl, dimethylbenzoyl, carboxybenzoyl, aminobenzoyl, methoxybenzoyl, chlorobenzoyl, dimethoxybenzoyl, trimethoxybenzoyl, methylenedioxybenzoyl, phenylbenzoyl, naphthoyl, methylnaphthoyl, methoxynaphthoyl, ethoxynaphthoyl, tetrahydronaphthoyl, acetylnaphthoyl, phenylacetyl, phenylpropionyl, phenylbutyryl, hydroxyphenylacetyl, methoxyphenylacetyl, acetyloxyphenylacetyl, aminophenylacetyl, fluorophenylacetyl, chlorophenylacetyl, bromophenylacetyl, methylthiophenylacetyl, methylphenylacetyl, dimethylphenylacetyl, naphthylacetyl, thienylacetyl, tetrazolylacetyl, methoxycarbonyl, ethoxycarbonyl, t-butoxycarbonyl, cyclohexyloxycarbonyl, chloroethoxycarbonyl, trichloroethoxycarbonyl, tribromoethoxycarbonyl, bromoethoxycarbonyl, iodoethoxycarbonyl, cyclopropylmethoxycarbonyl, cyclopropylethoxycarbonyl, cyclopentyloxycarbonyl, cyclohexyloxycarbonyl, cycloheptyloxycarbonyl, cyclohexadienyloxycarbonyl, isobornyloxycarbonyl, methanesulfonylethoxycarbonyl, ethanesulfonylpropoxycarbonyl, phenoxycarbonyl, methylphenoxycarbonyl, dimethylphenoxycarbonyl, diphenylmethoxycarbonyl, naphthyloxycarbonyl, benzyloxycarbonyl, bromobenzyloxycarbonyl, chlorobenzyloxycarbonyl, nitrobenzyloxycarbonyl, dimethylbenzyloxycarbonyl, methylenedioxybenzyloxycarbonyl, methanesulfonyl, ethanesulfonyl, benzenesulfonyl, methylbenzenesulfonyl, and benzylsulfonyl; COB is lower alkoxycarbonyl or aralkoxycarbonyl; Q is hydrogen, $C_1$ to $C_5$ alkyl, phenyl, tolyl, methoxylphenyl, chlorophenyl or isopropylphenyl; and Z is a hydrogen or a nucleophilic group selected from the group consisting of halogen, alkoxy, aralkoxy, aryloxy, hydroxy, alkylthio, aralkylthio, arylthio, mercapto, sulfo, alkylsulfonyl, amino, acetoxy, propionyloxy, butyryloxy, isobutyryloxy, pivaloyloxy, cyclobutylcarboxy, carbamoyloxy, methylcarbamoyloxy, ethylcarbamoyloxy, chloroethylcarbamoyloxy, trichloroethyoxycarbamoyloxy, dimethylcarbamoyloxy, di-(methoxybenzyl)-carbamoyloxy, phenylcarbamoloxy, anisylcarbamoyloxy, sulfophenylcarbamoyloxy, carboxymethylphenylcarbamoyloxy, methanesulfonyloxy, sulfonyloxy, thiopropionylthio, propylthiocarbonylthio, cyclopentyloxythiocarbonylthio, thiocarbamoylthio, dimethylthiocarbamoylthio, tosylthio, furylcarbonylthio, methylamino, ethylamino, diethylamino, chloroethylamino, anilino, tolylamino, methylnitrophenylamino, naphthylamino, methylpyrrolyl, pyridazinyl, and triazinyl, said nucleophilic groups which contain carbon atoms containing up to 10 carbon atoms.

2. A compound of the following formula:

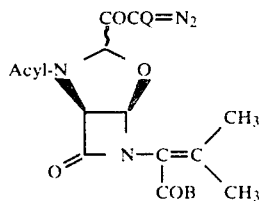

wherein Acyl is a member selected from the group consisting acetyl, cyclopentylcarbonyl, cyclopentylacetyl, cyclohexylcarbonyl, cyclohexylacetyl, cyclohexylpropionyl, cyclohexadienylacetyl, cycloheptylcarbonyl, cycloheptylacetyl, cycloheptylpropionyl, chloroacetyl, chloropropionyl, fluoroacetyl, bromoacetyl, difluoroacetyl, dichloroacetyl, chloropropionyl, hexenoyl, methoxyacetyl, isopropoxyacetyl, pentyloxyacetyl, hexyloxyacetyl, cyclohexyloxyacetyl, phenoxyacetyl, phenoxypropionyl, phenoxybutyryl, diphenoxyacetyl, methylthiophenoxyacetyl, tetrahydronaphthyloxyacetyl, methylthioacetyl, butylthioacetyl, cyclohexylthioacetyl, phenylthioacetyl, phenylthiopropionyl, fluorophenylthioacetyl, chlorophenylthioacetyl, pyridylthioacetyl, pyrimidylthioacetyl, benzoyl, methylbenzoyl, dimethylbenzoyl, carboxybenzoyl, aminobenzoyl, methoxybenzoyl, chlorobenzoyl, dimethoxybenzoyl, trimethoxybenzoyl, methylenedioxybenzoyl, phenylbenzoyl, naphthoyl, methylnaphthoyl, methoxynaphthoyl, ethoxynaphthoyl, tetrahydronaphthoyl, acetylnaphthoyl, phenylacetyl, phenylpropionyl, phenylbutyryl, hydroxyphenylacetyl, methoxyphenylacetyl, acetyloxyphenylacetyl, aminophenylacetyl, fluorophenylacetyl, chlorophenylacetyl, bromophenylacetyl, methylthiophenylacetyl, methylphenylacetyl, dimethylphenylacetyl, naphthylacetyl, thienylacetyl, tetrazolylacetyl, methoxycarbonyl, ethoxycarbonyl, t-butoxycarbonyl, cyclohexyloxycarbonyl, chloroethoxycarbonyl, trichloroethoxycarbonyl, tribromoethoxycarbonyl, bromoethoxycarbonyl, iodoethoxycarbonyl, cyclopropylmethoxycarbonyl, cyclopropylethoxycarbonyl, cyclopentyloxycarbonyl, cyclohexyloxycarbonyl, cycloheptyloxycarbonyl, cyclohexadienyloxycarbonyl, isobornyloxycarbonyl, methanesulfonylethoxycarbonyl, ethanesulfonylpropoxycarbonyl, phenoxycarbonyl, methylphenoxycarbonyl, dimethylphenoxycarbonyl, diphenylmethoxycarbonyl, naphthyloxycarbonyl, benzyloxycarbonyl, bromobenzyloxycarbonyl, chlorobenzyloxycarbonyl, nitrobenzyloxycarbonyl, dimethylbenzyloxycarbonyl, methylenedioxybenzyloxycarbonyl, methanesulfonyl, ethanesulfonyl, benzenesulfonyl, methylbenzenesulfonyl, and benzylsulfonyl; COB is lower alkoxycarbonyl or aralkoxycarbonyl; Q is hydrogen, $C_1$ to $C_5$ alkyl, phenyl, tolyl, methoxylphenyl, chlorophenyl or isopropylphenyl.

3. A compound according to claim 2, wherein Q is hydrogen.

4. A compound according to claim 3, wherein COB is benzyloxycarbonyl, and Acyl is phenylacetyl, benzoyl, carbobenzoxy, or benzylsulfonyl.

5. A compound according to claim 3, wherein COB is methoxycarbonyl and Acyl is phenylacetyl.

6. A compound according to claim 3, wherein COB is diphenylmethoxycarbonyl and Acyl is phenylacetyl.

7. A compound according to claim 1, wherein Q is hydrogen.

8. A compound according to claim 7, wherein Z is hydrogen, acetoxy, or chlorine.

9. A compound according to claim 8, wherein COB is benzyloxycarbonyl, Acyl is phenylacetyl, benzoyl, carbobenzoxy, or benzylsulfonyl, and Z is hydrogen, chlorine, or acetoxy.

10. A compound according to claim 8, wherein COB is methoxycarbonyl, Acyl is phenylacetyl, and Z is hydrogen or chlorine.

11. A compound according to claim 8, wherein COB is diphenylmethoxycarbonyl, Acyl is phenylacetyl, and Z is hydrogen or chlorine.

* * * * *